(12) United States Patent
Tobin

(10) Patent No.: US 11,718,856 B2
(45) Date of Patent: *Aug. 8, 2023

(54) RECOMBINANT MICELLE AND METHOD OF IN VIVO ASSEMBLY

(71) Applicant: Mozza Foods, Inc., Los Angeles, CA (US)

(72) Inventor: Cory J. Tobin, Pasadena, CA (US)

(73) Assignee: MOZZA FOODS, INC., Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/717,000

(22) Filed: Apr. 8, 2022

(65) Prior Publication Data

US 2022/0325292 A1    Oct. 13, 2022

Related U.S. Application Data

(63) Continuation of application No. 16/741,680, filed on Jan. 13, 2020, now Pat. No. 11,326,176.

(60) Provisional application No. 62/939,247, filed on Nov. 22, 2019.

(51) Int. Cl.
    *C12N 15/82* (2006.01)
    *B01D 61/14* (2006.01)

(52) U.S. Cl.
    CPC ....... *C12N 15/8202* (2013.01); *B01D 61/145* (2013.01); *B01D 61/146* (2022.08); *B01D 61/147* (2013.01); *C12N 15/8218* (2013.01); *B01D 2315/16* (2013.01)

(58) Field of Classification Search
    CPC .................................................. C12N 15/82
    See application file for complete search history.

(56) References Cited

U.S. PATENT DOCUMENTS

| | | |
|---|---|---|
| 4,518,616 A | 5/1985 | Czulak |
| 5,015,580 A | 5/1991 | Christou et al. |
| 5,159,135 A | 10/1992 | Umbeck |
| 5,491,084 A | 2/1996 | Chalfie et al. |
| 5,538,880 A | 7/1996 | Lundquist et al. |
| 5,547,870 A | 8/1996 | Datta et al. |
| 5,550,318 A | 8/1996 | Adams et al. |
| 5,591,616 A | 1/1997 | Hiei et al. |
| 5,599,670 A | 2/1997 | Jefferson |
| 5,633,435 A | 5/1997 | Barry et al. |
| 5,780,708 A | 7/1998 | Lundquist et al. |
| 5,824,877 A | 10/1998 | Hinchee et al. |
| 6,118,047 A | 9/2000 | Anderson et al. |
| 6,153,812 A | 11/2000 | Fry et al. |
| 6,160,208 A | 12/2000 | Lundquist et al. |
| 6,194,636 B1 | 2/2001 | McElroy et al. |
| 6,232,526 B1 | 5/2001 | McElroy et al. |
| 6,288,312 B1 | 9/2001 | Christou et al. |
| 6,384,301 B1 | 5/2002 | Martinell et al. |
| 6,399,861 B1 | 6/2002 | Anderson et al. |
| 6,541,682 B1 | 4/2003 | Nehra et al. |
| 6,603,061 B1 | 8/2003 | Armstrong et al. |
| 6,632,468 B2 | 10/2003 | Morgan et al. |
| 7,417,178 B2 * | 8/2008 | Huang ............... C12N 15/8234 800/320.2 |
| 11,076,615 B2 * | 8/2021 | Pandya ............... A23C 9/1315 |
| 11,326,176 B2 | 5/2022 | Tobin |
| 2003/0044503 A1 | 3/2003 | Morgan et al. |
| 2004/0216189 A1 | 10/2004 | Houmard et al. |
| 2005/0166289 A1 | 7/2005 | Chuan Chiang et al. |
| 2005/0172356 A1 | 8/2005 | Christeller et al. |
| 2010/0048464 A1 | 2/2010 | Recio Sanchez et al. |
| 2010/0223682 A1 | 9/2010 | Katz et al. |
| 2011/0293813 A1 | 12/2011 | Cavallini et al. |
| 2013/0065824 A1 | 3/2013 | De Kort et al. |
| 2013/0295646 A1 | 11/2013 | Lejars et al. |
| 2016/0168198 A1 | 6/2016 | Govindappa et al. |
| 2017/0164632 A1 | 6/2017 | Pandya et al. |
| 2017/0273328 A1 | 9/2017 | Pandya et al. |
| 2018/0291392 A1 | 10/2018 | El-Richani et al. |
| 2019/0216106 A1 | 7/2019 | Geistlinger et al. |

(Continued)

FOREIGN PATENT DOCUMENTS

| | | |
|---|---|---|
| CN | 101305017 A | 11/2008 |
| CN | 101600358 A | 12/2009 |

(Continued)

OTHER PUBLICATIONS

Philip et al 2001 Plant Science 161:323-335 (Year: 2001).*
Co-pending U.S. Appl. No. 17/826,021, inventors Tobin; Cory J et al., filed May 26, 2022.
PCT/US2020/056449 International Search Report and Written Opinion dated Feb. 3, 2021.
Philip et al.: Processing and localization of bovine beta-casein expressed in transgenic soybean seeds under control of a soybean lectin expression cassette. [Abstract Only] Plant Sci. 161(2):323-335 doi:10.1016/s0168-9452(01)00420-4 (2001).
Philip et al.: Processing and localization of bovine beta-casein expressed in transgenic soybean seeds under control of a soybean lectin expression cassette. Plant Sci. 161(2):323-335 doi:10.1016/s0168-9452(01)00420-4 (2001).

*Primary Examiner* — Brent T Page
(74) *Attorney, Agent, or Firm* — Wilson Sonsini Goodrich & Rosati

(57) ABSTRACT

A method of in vivo assembly of a recombinant micelle including: introducing a plasmid into a plant cell, wherein: the plasmid includes a segment of deoxyribonucleic acid (DNA) for encoding a ribonucleic acid (RNA) for a protein in a casein micelle, the segment of DNA is transcribed and translated; forming recombinant casein proteins in the plant cell, wherein: the recombinant casein proteins include a κ-casein and at least one of an $\alpha S_1$-casein, an $\alpha S_2$-casein, a β-casein; and assembling in vivo a recombinant micelle within the plant cell, wherein: an outer layer of the recombinant micelle is enriched with the κ-casein, an inner matrix of the recombinant micelle include at least one of the $\alpha S_1$-casein, the $\alpha S_2$-casein, the β-casein.

14 Claims, 10 Drawing Sheets

Specification includes a Sequence Listing.

(56) References Cited

U.S. PATENT DOCUMENTS

| | | |
|---|---|---|
| 2021/0037849 A1 | 2/2021 | Pandya et al. |
| 2021/0115456 A1 | 4/2021 | Mason et al. |
| 2021/0198693 A1 | 7/2021 | Mason et al. |
| 2021/0235714 A1 | 8/2021 | Geistlinger et al. |

FOREIGN PATENT DOCUMENTS

| | | |
|---|---|---|
| CN | 102883623 A | 1/2013 |
| WO | WO-2021050759 A2 | 3/2021 |
| WO | WO-2021101647 A1 | 5/2021 |

* cited by examiner

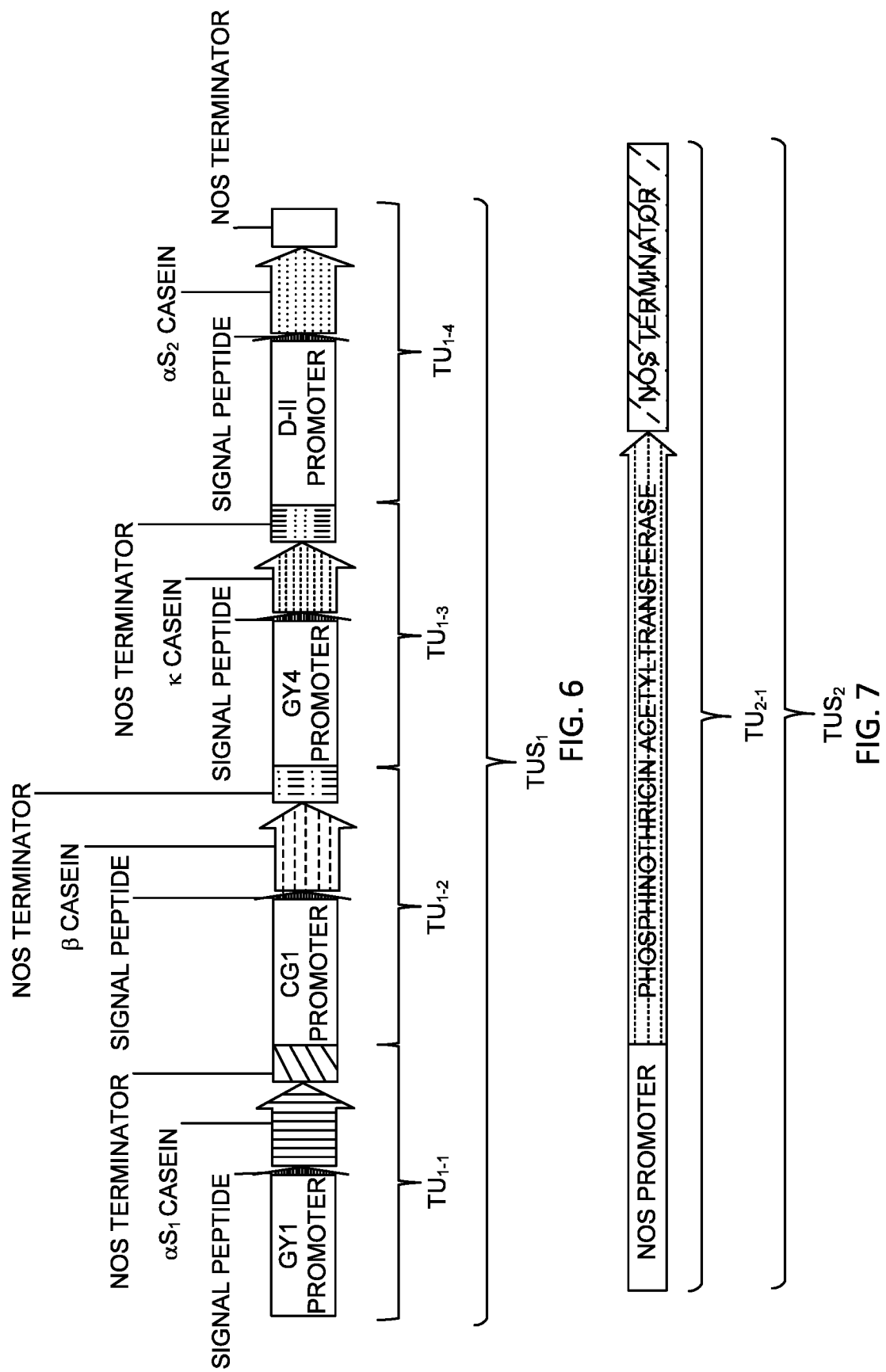

RECOMBINANT MICELLE AND METHOD OF IN VIVO ASSEMBLY

SEQUENCE LISTING

The content of the ASCII text file of the sequence listing named "Mozza 62162-701_301_Sequence_Listing.txt", which is 30,917 bytes in size was created on Apr. 6, 2022 and electronically submitted via EFS-Web on Apr. 8, 2022, is incorporated herein by reference in its entirety.

CROSS REFERENCE TO RELATED APPLICATIONS

This application is a continuation of U.S. application Ser. No. 16/741,680, filed Jan. 13, 2020, which claims the benefit of U.S. Provisional Patent Application No. 62/939,247, filed Nov. 22, 2019, all of which are incorporated herein by reference in their entireties.

TECHNICAL FIELD

An embodiment of the present disclosure relates generally to a micelle and more particularly to recombinant micelle and method of in vivo assembly in a plant cell.

BACKGROUND

Casein micelles account for more than 80% of the protein in bovine milk and are a key component of all dairy cheeses. Casein micelles include individual casein proteins are produced in the mammary glands of bovines and other ruminants. The industrial scale production of the milk that is processed to yield these casein micelles, primarily in the form of curds for cheese production, typically occurs on large-scale dairy farms and is often inefficient, damaging to the environment, and harmful to the animals. Dairy cows contribute substantially to greenhouse gasses, consume significantly more water than the milk they produce, and commonly suffer from dehorning, disbudding, mastitis, routine forced insemination, and bobby calf slaughter.

Accordingly, there is a need for an in vivo plant-based casein expression system which allows for purification of biologically active casein proteins that is cost effective at industrial scale.

Solutions to these problems have been long sought but prior developments have not taught or suggested any solutions and, thus, solutions to these problems have long eluded those skilled in the art.

DISCLOSURE OF INVENTION

An embodiment of the present invention provides a method of in vivo assembly of a recombinant micelle including: introducing a plasmid into a plant cell, wherein: the plasmid includes a segment of deoxyribonucleic acid (DNA) for encoding a ribonucleic acid (RNA) for a protein in a casein micelle, the segment of DNA is transcribed and translated; forming recombinant casein proteins in the plant cell, wherein: the recombinant casein proteins include a κ-casein and at least one of an $\alpha S_1$-casein, an $\alpha S_2$-casein, a β-casein; and assembling in vivo a recombinant micelle within the plant cell, wherein: an outer layer of the recombinant micelle is enriched with the κ-casein, an inner matrix of the recombinant micelle include at least one of the $\alpha S_1$-casein, the $\alpha S_1$-casein, the β-casein.

An embodiment of the present invention provides a recombinant micelle including: an outer layer enriched with a κ-casein; and an inner matrix including at least one of a $\alpha S_1$-casein, a $\alpha S_1$-casein, a β-casein.

An embodiment of the present invention provides a plasmid including a segment of deoxyribonucleic acid (DNA) for encoding a protein in a casein micelle wherein the segment of DNA includes a promoter and a N-terminal signal peptide.

Certain embodiments of the disclosure have other steps or elements in addition to or in place of those mentioned above. The steps or elements will become apparent to those skilled in the art from a reading of the following detailed description when taken with reference to the accompanying drawings.

BRIEF DESCRIPTION OF THE DRAWINGS

FIG. 6 is an example of a schematic illustration of a portion of a plasmid in soybean.

FIG. 7 is an example of a schematic illustration of a portion of a plasmid in soybean for herbicide resistance in plants.

DETAILED DESCRIPTION

Figure 1:
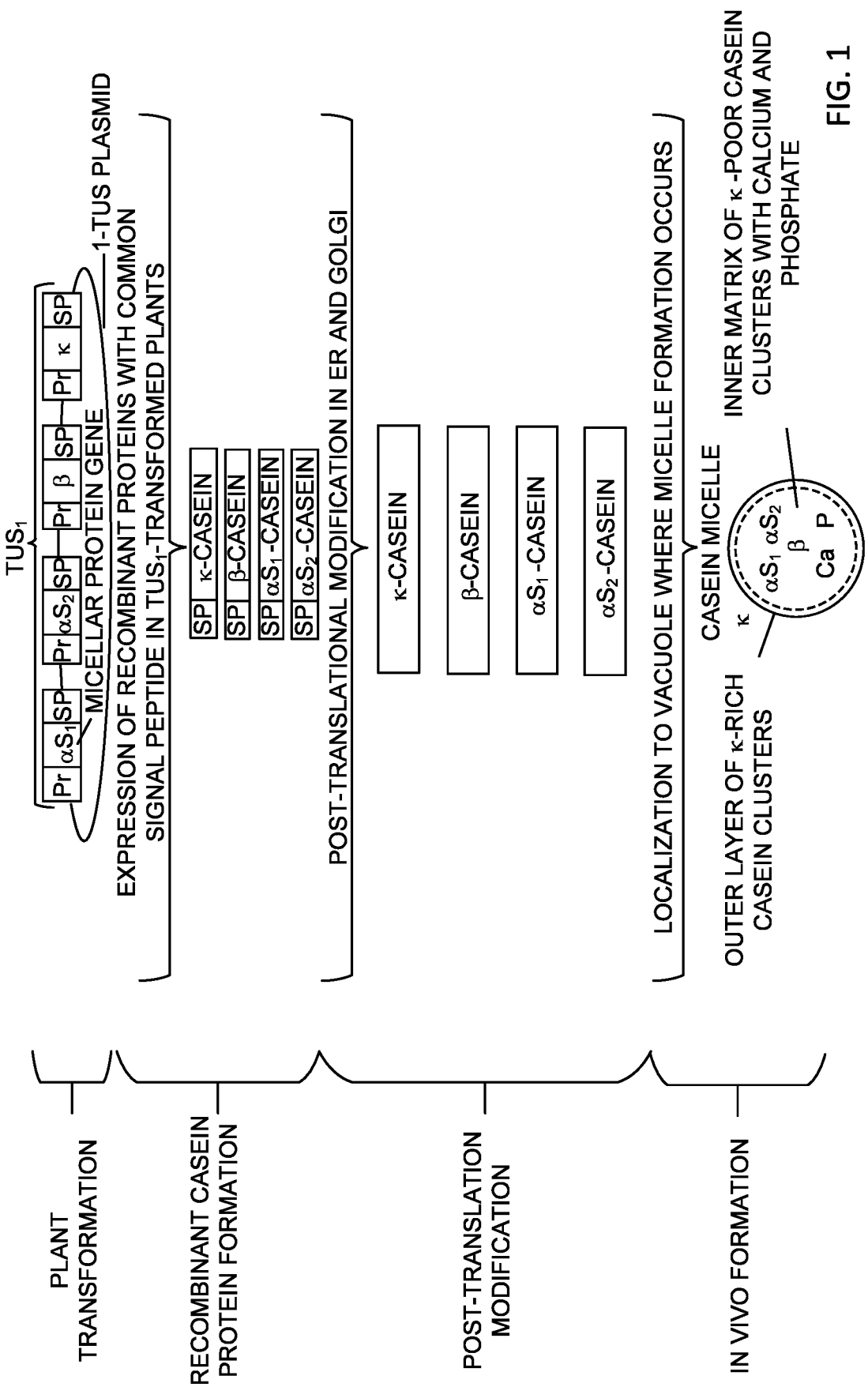
FIG. 1 is an example of a flow for forming in vivo casein micelles in an embodiment.

The following embodiments are described in sufficient detail to enable those skilled in the art to make and use the invention. It is to be understood that other embodiments would be evident based on the present disclosure, and that system, process, or mechanical changes may be made without departing from the scope of an embodiment of the present disclosure.

In the following description, numerous specific details are given to provide a thorough understanding of the invention. However, it will be apparent that the invention may be practiced without these specific details. In order to avoid obscuring an embodiment of the present disclosure, some well-known techniques, system configurations, and process steps are not disclosed in detail.

The drawings showing embodiments of the system are semi-diagrammatic, and not to scale and, particularly, some of the dimensions are for the clarity of presentation and are shown exaggerated in the drawing figures. Similarly, although the views in the drawings for ease of description generally show similar orientations, this depiction in the figures is arbitrary for the most part. Generally, the invention can be operated in any orientation.

The term "invention" or "present invention" as used herein is not meant to be limiting to any one specific embodiment of the invention but applies generally to any and all embodiments of the invention as described in the claims and specification.

Referring now to FIG. 1, therein is shown an example of a flow for forming in vivo casein micelles in an embodiment. In this example, FIG. 1 depicts the flow for forming the casein micelles by a plant transformation, a recombinant casein protein formation, a post-translation modification, and an in-vivo formation. As a specific example, FIG. 1 is a schematic illustration of the elements of a plasmid of this embodiment and its use in creation of micelles in vivo in a plant cell.

In this example for the plant transformation, a plant is transformed using a plasmid including a single transcription unit set. As used herein "plasmid" is a deoxyribonucleic acid (DNA) molecule capable of replication in a host cell and to which another DNA segment can be operatively linked so as to bring about replication of the attached DNA segment. As it relates to this example, methods for plant transformation include microprojectile bombardment as illustrated in U.S. Pat. Nos. 5,015,580; 5,550,318; 5,538,880; 6,153,812; 6,160,208; 6,288,312 and 6,399,861, all of which are incorporated herein by reference. Methods for plant transformation also include *Agrobacterium*-mediated transformation as illustrated in U.S. Pat. Nos. 5,159,135; 5,824,877; 5,591,616 and 6,384,301, all of which are incorporated herein by reference. Recipient cells for the plant transformation include, but are not limited to, meristem cells, callus, immature embryos, hypocotyls explants, cotyledon explants, leaf explants, and gametic cells such as microspores, pollen, sperm and egg cells, and any cell from which a fertile plant may be regenerated, as described in U.S. Pat. Nos. 6,194,636; 6,232,526; 6,541,682 and 6,603,061 and U.S. Patent Application publication US 2004/0216189 A1, all of which are incorporated herein by reference.

Continuing this example for the plant transformation, the plasmid including the single transcription unit set is shown and abbreviated in FIG. 1 as 1-TUS PLASMID. The transcription unit set included on this plasmid is transcription unit set 1 shown and abbreviated in FIG. 1 as $TUS_1$. As used herein "transcription unit set" is a segment of DNA including one or more transcription units. The purpose of a transcription unit set includes but is not limited to protein expression, gene suppression, regulatory ribonucleic acid (RNA) production, and herbicide resistance. As used herein "transcription unit" is a segment of DNA including at least a promoter DNA and transcribable DNA. As used herein "promoter" means regulatory DNA for initiating RNA transcription. A "plant promoter" is a promoter capable of initiating transcription in plant cells whether or not its origin is a plant cell. As used herein "terminator" means any DNA sequence that causes RNA transcription to terminate.

Further continuing this example for the plant transformation shown in FIG. 1 as an embodiment, the transcription unit set 1 includes four segments of DNA; each encoding RNA for one of the four proteins found in a casein micelle: an $\alpha S_1$ casein, an $\alpha S_2$ casein, a β casein, and a κ casein. For clarity and as an example, the genes encoding the $\alpha S_1$ casein, the $\alpha S_2$ casein, the β casein, and the κ casein are shown and abbreviated in FIG. 1 as $\alpha S_1$, as $\alpha S_2$, as (3, and as κ, respectively, and shown and annotated in FIG. 1 as MICELLAR PROTEIN GENE. Each DNA segment encoding RNA for one of the four proteins found in a casein micelle is operably linked to a promoter, shown and abbreviated in FIG. 1 as P, and includes a plant-derived, tissue specific, N-terminal signal peptide, shown and abbreviated in FIG. 1 as SP. As used herein "operably linked" is the association of two or more DNA fragments in a DNA construct such that the function of one is controlled by the other, for example DNA encoding a protein associated with DNA encoding a promoter. In some embodiments, the N-terminal signal peptide targets the recombinant casein proteins to the plant vacuoles. In other embodiments, the recombinant casein proteins are targeted to and retained in the endoplasmic reticulum.

As an example for the recombinant casein protein formation, when the four segments of DNA included in transcription unit set 1 are transcribed and translated in a transgenic plant (not shown), four recombinant casein proteins, each including a plant-derived tissue specific signal peptide, are formed in the cytoplasm of the plant cell. The recombinant casein proteins are shown and abbreviated in FIG. 1 as $\alpha S_1$-CASEIN, as $\alpha S_2$-CASEIN, as β-CASEIN, and as κ-CASEIN, respectively, and are also referred to herein as "recombinant casein proteins" for brevity. As used herein, "transgenic" plant is a plant whose genome has been altered by the stable integration of recombinant DNA. As an example of stable integration, the transgenic plant includes a plant regenerated from an originally-transformed plant cell and progeny transgenic plants from later generations or crosses of a transformed plant. As used herein "recombinant DNA" refers to DNA which has been synthesized, assembled or constructed outside of a cell. Examples of recombinant DNA can include DNA containing naturally occurring DNA or complementary DNA (cDNA) or synthetic DNA.

As it relates to this example for the post-translation modification shown in FIG. 1 as an embodiment, the four recombinant casein proteins in the cytoplasm of the plant cell include the $\alpha S_1$-casein, the $\alpha S_2$-casein, the β-casein, and the κ-casein, each including a signal peptide (SP) that localizes the recombinant casein protein to specific organelles, for example the secretory pathway and protein storage vacuoles, in the plant cell. The signal peptide is removed from the recombinant casein proteins during post-translational modification that occurs in the endoplasmic reticulum and the Golgi apparatus of the plant cell. For clarity in this example, the endoplasmic reticulum and the Golgi apparatus are shown and abbreviated in FIG. 1 as ER, and as GOLGI, respectively. In this embodiment and example, phosphorylation occurs on the recombinant casein proteins prior to, during, or after migration to a specific tissue, shown in FIG. 1 as circles enclosing the letter "P" attached to each of the recombinant casein proteins. In other embodiments and examples, one or more post-translational modifications of the recombinant casein proteins can occur, including phosphorylation, glycosylation, ubiquitination, nitrosylation, methylation, acetylation, lipidation and proteolysis. In other embodiments no post-translational modifications occur on the recombinant casein proteins, or in other words, the post-translation modification is optional.

Continuing this example for the in vivo formation as an embodiment, an outer layer of the micelle is enriched in recombinant κ-casein shown and abbreviated in FIG. 1 as κ, and an inner matrix of the micelle includes the recombinant $\alpha S_1$-casein, the recombinant $\alpha S_2$-casein, the recombinant β-casein, the calcium and the phosphate, shown in and annotated in FIG. 1 as $\alpha S_1$, $\alpha S_2$, as $\alpha S$, and β, respectively. Micelle formation is enhanced by the presence of intracellular calcium and phosphate, shown and abbreviated in FIG. 1 as Ca and P, respectively.

Figure 2:
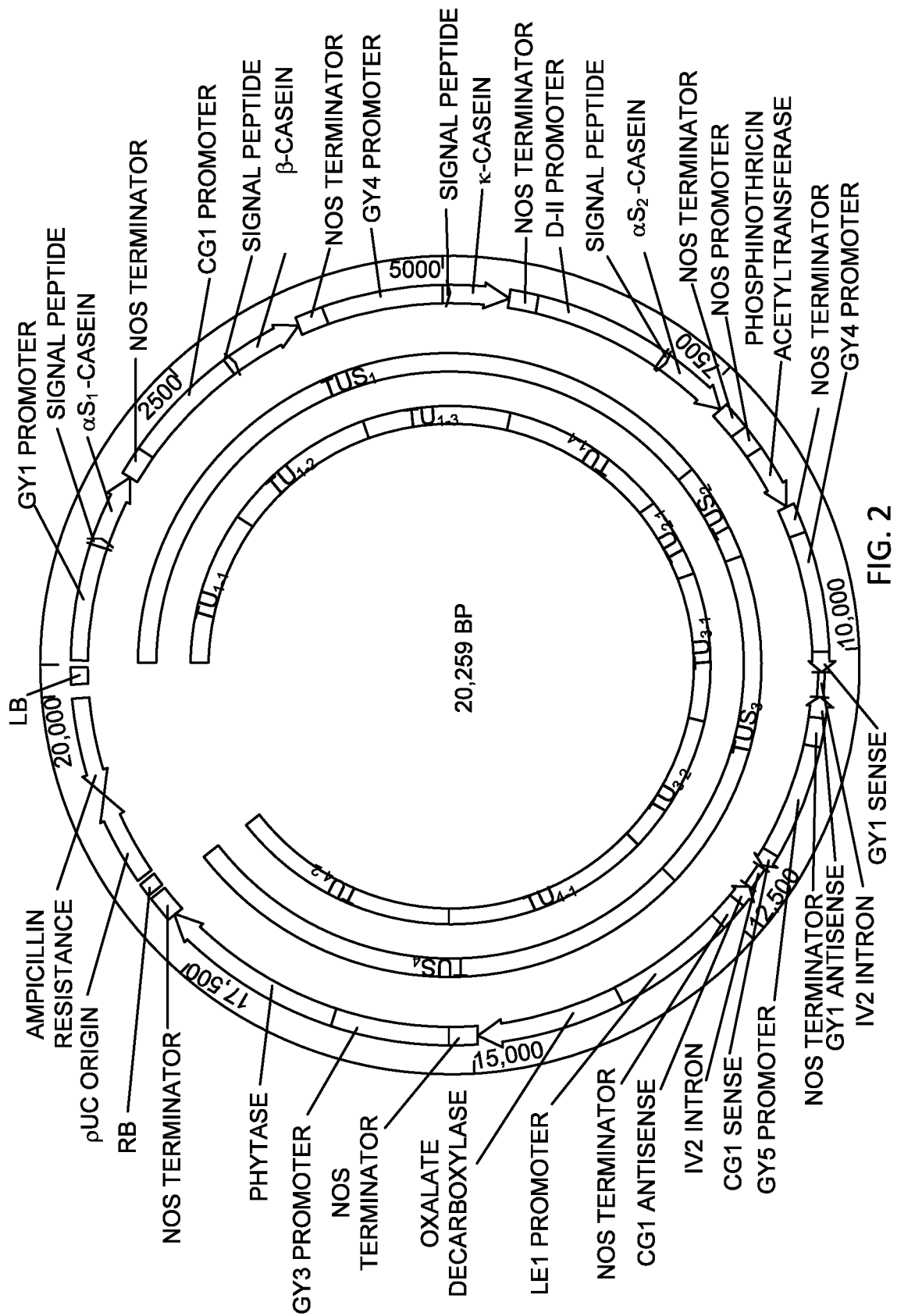
FIG. 2 is an example of a schematic illustration of a plasmid used in FIG. 1.

Referring now to FIG. 2, therein is shown an example of a schematic illustration of a plasmid used in FIG. 1. As a specific example, FIG. 2 is a schematic illustration of the elements of a plasmid of this embodiment.

In this example for the plant transformation of FIG. 1, an embodiment provides a plant that is transformed with one or more transfer DNAs including one or more transcription unit sets. As used herein "transfer DNA" (T-DNA) is DNA which integrates or is integrated into a genome.

For example, an *Agrobacterium*-mediated transformation T-DNA is part of a binary plasmid, which is flanked by T-DNA borders, and the binary plasmid is transferred into an *Agrobacterium tumefaciens* strain carrying a disarmed tumor inducing plasmid. Also for example, for a biolistic mediated transformation a gene gun is used for delivery of T-DNA, which is typically a biolistic construct containing promoter and terminator sequences, reporter genes, and border sequences or signaling peptides, to cells.

Continuing the example of a T-DNA used to transform a plant in an embodiment, the T-DNA includes four transcription unit sets: a transcription unit set 1, a transcription unit set 2, a transcription unit set 3, and a transcription unit set 4. For clarity, the transcription unit set 1, the transcription unit set 2, the transcription unit set 3, and the transcription unit set 4 are shown and abbreviated in FIG. 2 as $TUS_1$, as $TUS_2$, as $TUS_3$, and as $TUS_4$, respectively.

In this example as an embodiment, $TUS_1$ includes one transcription unit for each of the four casein proteins found in a casein micelle of FIG. 2: a transcription unit 1-1 includes DNA encoding $\alpha S_1$-casein, a transcription unit 1-2 includes DNA encoding β-casein, a transcription unit 1-3 includes DNA encoding κ-casein, and a transcription unit 1-4 includes DNA encoding $\alpha S_1$-casein. For clarity and brevity, the transcription unit 1-1, the transcription unit 1-2, the transcription unit 1-3, and the transcription unit 1-4 are shown and abbreviated in FIG. 2 as $TU_{1-1}$, as $TU_{1-2}$, as $TU_{1-3}$, and as $TU_{1-4}$, respectively. Each transcription unit in $TUS_1$ can also include DNA encoding the same plant-derived signal peptide. Additionally, each transcription unit in $TUS_1$ includes a promoter and a transcriptional terminator.

Continuing this example as an embodiment, $TUS_2$ includes one transcription unit, shown and abbreviated in FIG. 2 as $TU_{2-1}$, that includes a promoter, DNA encoding phosphinothricin acetyltransferase, and a transcriptional terminator. In other embodiments, $TUS_2$ can include one or more genes encoding a selectable marker that can impart herbicide or antibiotic resistance which enables the selection of transformed plants that produce micelles in vivo. Genes enabling selection of transformed plants include those conferring resistance to antibiotics, including as examples kanamycin, hygromycin B, gentamicin, and bleomycin. Genes enabling selection of transformed plants also include those conferring resistance to herbicides, including as examples a glyphosate herbicide, a phosphinothricin herbicide, an oxynil herbicide, an imidazolinone herbicide, a dinitroaniline herbicide, a pyridine herbicide, a sulfonylurea herbicide, a bialaphos herbicide, a sulfonamide herbicide, and a glufosinate herbicide. Examples of such selectable markers are illustrated in U.S. Pat. Nos. 5,550,318; 5,633,435; 5,780,708 and 6,118,047, all of which are incorporated herein by reference. In other embodiments, $TUS_2$ includes one or more genes expressing a screenable marker which enables the visual identification of transformed plants that produce micelles in vivo. Genes expressing a screenable marker include genes encoding a colored or fluorescent protein, including as examples luciferase or green fluorescent protein (U.S. Pat. No. 5,491,084, herein incorporated by reference), and genes expressing β-glucuronidase or uidA gene (U.S. Pat. No. 5,599,670, herein incorporated by reference) for which various chromogenic substrates are known. In some embodiments, each of the genes encoding a selectable or screenable marker are operably linked to an inducible promoter, such as for example a NOS promoter, or a tissue-specific promoter, such as for example a promoter from the soybean a' subunit of β-conglycinin, such that the translation of the selectable or screenable markers can be regulated.

Continuing this example as an embodiment, $TUS_3$ includes two transcription units that yield untranslated RNA molecules that suppress native seed protein gene translation. The first transcription unit in $TUS_3$, a transcription unit 3-1, includes the sense strand, or coding strand, of DNA encoding soybean Glycinin1, and the antisense strand, or non-coding strand, of DNA encoding soybean Glycinin1 separated by the potato IV2 intron. For clarity and brevity, the transcription unit 3-1 the sense strand or coding strand of DNA encoding soybean Glycinin1, and the antisense strand or non-coding strand of DNA encoding soybean Glycinin1, the potato IV2 intron are shown and annotated in FIG. 2 as $TU_{3-1}$ as GY1 SENSE, as GY1 ANTISENSE, and as IV2 INTRON, respectively. The second transcription unit in $TUS_3$, a transcription unit 3-2 includes the sense strand, or coding strand, of DNA encoding β-conglycinin 1 and the antisense strand, or non-coding strand, of DNA encoding (3-conglycinin 1 separated by the potato IV2 intron. For clarity and brevity, the transcription unit 3-2, the sense strand or coding strand of DNA encoding β-conglycinin 1, the antisense strand or non-coding strand of DNA encoding β-conglycinin 1, and the potato IV2 intron are shown and annotated in FIG. 2 as $TU_{3-2}$ as CG1 SENSE, as CG1 ANTISENSE, and as IV2 INTRON, respectively.

In other embodiments, $TUS_3$ includes other transcription units that yield untranslated RNA molecules that suppress native seed protein gene translation. As an example, in other embodiments, $TUS_3$ includes one transcription unit, a transcription unit 3-1, that includes a promoter from the soybean GY4 gene (SEQ ID NO:15), a miR319a microRNA from *Arabidopsis thaliana* that has been modified such that the homologous arms of the microRNA hairpin contain 21 nucleotide sequences matching a portion of the soybean GY1 gene sequence (SEQ ID NO:10), and a NOS transcriptional terminator (SEQ ID NO:35) (not shown).

Continuing this example as an embodiment, $TUS_4$ includes two transcription units that encode proteins which alter the intracellular environment in a manner that optimizes the production of micelles having requisite attributes including size, mineral content, protein content, protein distribution, and mass. The first transcription unit in $TUS_4$, a transcription unit 4-1 includes a promoter, DNA encoding oxalate decarboxylase, and a transcriptional terminator. For clarity and brevity, the transcription unit 4-1 is shown and abbreviated in FIG. 2 as $TU_{4-1}$. The second transcription unit in $TUS_4$, a transcription unit 4-2, includes a promoter, DNA encoding phytase, and a transcriptional terminator. For clarity and brevity, the transcription unit 4-2 is shown and abbreviated as $TU_{4-2}$. In this embodiment, transcription and translation of $TU_{4-1}$ yields an oxalate-degrading enzyme which increases the amount of free intracellular calcium available for capture and inclusion during micelle formation. Also in this embodiment, transcription and translation of $TU_{4-2}$ yields a phytase enzyme which increases the amount of free intracellular phosphate available for capture and inclusion during micelle formation. In some embodiments, each of the genes encoding oxalate-degrading enzymes or phytase enzymes are operably linked to a constitutive promoter, tissue specific promoter or an inducible promoter, such as for example, a nopaline synthase promoter or a promoter from the soybean β-conglycinin gene, such that the translation of proteins which alter the intracellular environment can be regulated. In some embodiments, $TUS_4$ includes both a transcription unit 4-1 that increases the intracellular calcium concentration and a transcription unit 4-2 that increases the intracellular phosphate concentration. In other embodiments, $TUS_4$ includes only a transcription unit 4-1 that increases the intracellular calcium concentration. In other embodiments, $TUS_4$ includes only a transcription unit 4-2 that increases the intracellular phosphate concentration.

In other embodiments, $TUS_4$ includes transcription units that increase the intracellular calcium concentration by expressing an oxalate oxidase enzyme (not shown). As an example, in other embodiments, $TUS_4$ includes one transcription unit, a transcription unit 4-1, that includes a promoter from the soybean GY4 gene (SEQ ID NO:15), the coding sequence for the oxalate oxidase 1 coding sequence from wheat that has been codon optimized for expression in soybean (SEQ ID NO:9), and the NOS transcriptional terminator (SEQ ID NO:35) (not shown). In other embodiments, $TUS_4$ includes transcription units that increase the intracellular phosphate concentration by suppressing the expression of the soybean myo-inositol-3-phosphate synthase (MIPS1) gene. As an example, in other embodiments, $TUS_4$ includes one transcription unit, a transcription unit 4-2, that includes a promoter from the soybean GY4 gene (SEQ ID NO:15), a portion of the MIPS1 coding sequence lacking a start codon (SEQ ID NO:21), the IV2 intron from potato (SEQ ID NO:25), the antisense of the MIPS1 sequence (SEQ ID NO:22), and the NOS transcriptional terminator (SEQ ID NO:35) (not shown).

In some embodiments of the disclosure, transcription unit sets are assembled in numeric order. In other embodiments, transcription unit sets can be assembled in any order.

In some embodiments of the disclosure, the plant is transformed with a plasmid that contains transcription unit sets $TUS_1$, $TUS_2$, $TUS_3$, and $TUS_4$. In other embodiments of the disclosure, the plant is transformed with a plasmid that contains only transcription unit set $TUS_1$.

In some embodiments of the disclosure, the plant is transformed with a plasmid that contains transcription unit sets $TUS_1$, and $TUS_2$. In other embodiments of the disclosure, the plant is transformed with a plasmid that contains transcription unit sets $TUS_1$, $TUS_2$, and $TUS_3$. In other embodiments of the disclosure, the plant is transformed with a plasmid that contains transcription unit sets $TUS_1$, $TUS_2$, and $TUS_4$.

In other embodiments of the disclosure, the plant is transformed with a plasmid that contains transcription unit sets $TUS_1$, and $TUS_3$. In other embodiments of the disclosure, the plant is transformed with a plasmid that contains transcription unit sets $TUS_1$, $TUS_3$, and $TUS_4$.

In other embodiments of the disclosure, the plant is transformed with a plasmid that contains transcription unit sets $TUS_1$, and $TUS_4$. In some embodiments of the disclosure, transgenic plants are prepared by crossing a first plant that has been transformed with a plasmid containing one or more transcription unit sets with a second untransformed plant. In other embodiments of the disclosure, transgenic plants are prepared by crossing a first plant that has been transformed with a plasmid containing one or more but not all transcription unit sets required for micelle formation in vivo with a second plant having one or more transcription unit sets, wherein at least one of the transcription unit sets is present in the second plant and not present in the first plant.

In some embodiments of the disclosure, transgenic plants are prepared by crossing a first plant that has been transformed with a plasmid containing one or more transcription unit sets enabling micelle formation in vivo with a second plant having another trait, such as herbicide resistance or pest resistance.

In some embodiments of the disclosure, transgenic plants are prepared by growing progeny generations of a plant that has been transformed with a plasmid containing one or more transcription unit sets enabling micelle formation in vivo. In other embodiments, transgenic plants are prepared by growing progeny generations of a transgenic plant produced by crossing one or more plants that have been transformed with a plasmid containing one or more transcription unit sets enabling micelle formation in vivo.

Further to this example shown in FIG. 2 as an embodiment, the promoters in the four transcription unit sets include the promoters of genes coding for soybean Glycinin1, soybean β-conglycinin1, soybean Glycinin4, soybean Bowman-Birk protease inhibitor, *Agrobacterium* nopaline synthase, soybean Glycinin5, soybean lectin, and soybean Glycinin3. For clarity and brevity, the promoters of genes coding for soybean Glycinin1 is shown and annotated in FIG. 2 as GY1 PROMOTER. Also for clarity and brevity, the soybean β-conglycinin1 is shown and annotated in FIG. 2 as CG1 promoter. Further for clarity and brevity, the soybean Glycinin4 is shown and annotated in FIG. 2 as GY4 promoter. Yet further for clarity and brevity, the Bowman-Birk protease inhibitor promoter is shown and annotated in FIG. 2 as D-II promoter. Yet further for clarity and brevity, the *Agrobacterium* nopaline synthase is shown and annotated in FIG. 2 as NOS promoter. Yet further for clarity and brevity, the soybean Glycinin5 is shown and annotated in FIG. 2 as GY5 promoter. Yet further for clarity and brevity, the soybean lectin is shown and annotated in FIG. 2 as LE1 promoter. Yet further for clarity and brevity, the soybean Glycinin3 is shown and annotated in FIG. 2 as GY3 promoter.

In other embodiments and examples, promoters in one or more of the four transcription unit sets include a promoter capable of initiating transcription in plant cells whether or not an origin of the promoter is a plant cell. For example, *Agrobacterium* promoters are functional in plant cells. The promoters capable of initiating transcription in plant cells include promoters obtained from plants, plant viruses and bacteria such as *Agrobacterium*.

As specific examples of promoters under developmental control include promoters that preferentially initiate transcription in certain tissues, such as leaves, roots, or seeds. Such promoters are referred to as "tissue preferred". Also as specific examples of promoters that initiate transcription only in certain tissues are referred to as "tissue specific". Further as a specific example, a "cell type specific" promoter primarily drives expression in certain cell types in one or more organs, for example, vascular cells in roots or leaves. Yet further a specific example, an "inducible" or "repressible" promoter is a promoter which is under environmental control. Examples of environmental conditions that may affect transcription by inducible or repressible promoters include anaerobic conditions, or certain chemicals, or the presence of light. Tissue preferred, tissue specific, cell type specific, and inducible or repressible promoters constitute the class of "non-constitutive" promoters. A "constitutive" promoter is a promoter which is active under most conditions.

Returning to this example in FIG. 2 as an embodiment, the transcriptional terminators in the four transcription unit sets include the termination sequence of the nopaline synthase gene, shown and annotated in FIG. 2 as NOS terminator. In other embodiments, the transcriptional terminators in one or more of the four transcription unit sets includes transcriptional terminators from the native soybean Glycinin genes, or any other plant transcriptional terminators.

In this example as an embodiment, the T-DNA used to transform a plant also includes DNA encoding an origin of replication, a gene conferring antibiotic resistance, a right boundary for the T-DNA, and a left boundary for the T-DNA, shown and annotated in FIG. 2 as pUC origin, ampicillin resistance, RB, and LB, respectively. In this embodiment, the gene conferring antibiotic resistance is a gene conferring resistance to the antibiotic ampicillin. In other embodiments, the gene conferring antibiotic resistance is a gene conferring resistance to any other antibiotic, including kanamycin and chloramphenicol.

Figure 3A:
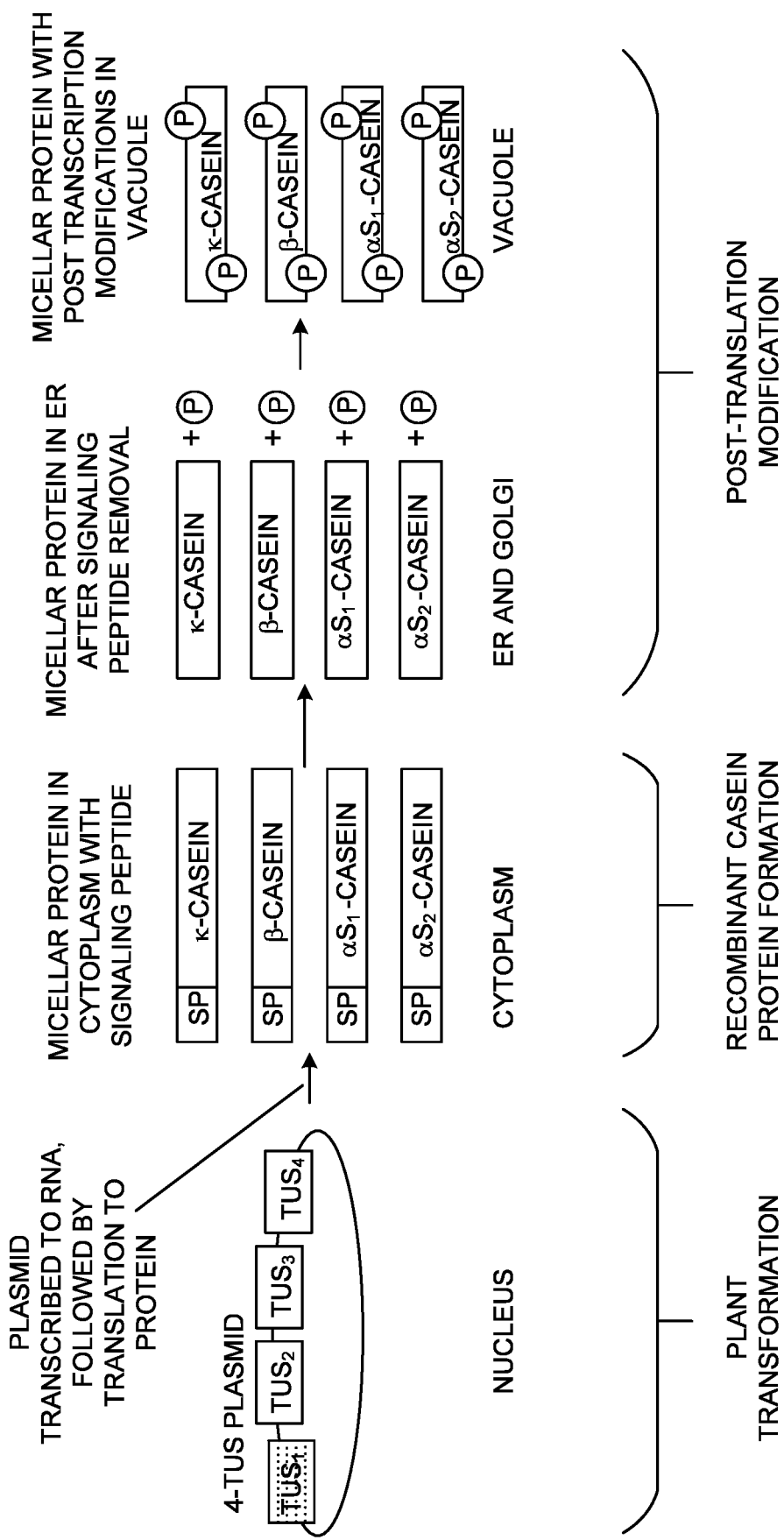
FIG. 3A is an example with additional details from the plant transformation to the post-translation modification.

Referring now to FIG. 3A, therein is shown an example with additional details from the plant transformation to the post-translation modification. The plant transformation and the post-translation modification are also described in FIG. 1. The example depicted in FIG. 3A also depicts the recombinant casein protein formation, also described in FIG. 1. As a specific example, FIG. 3A schematically illustrates the transcription of casein proteins from genes in $TUS_1$ as well as post transcriptional alterations that occur as the proteins move towards their subcellular specific destination encoded by the common signal peptide.

In the example shown in FIG. 3A, the purpose of transcription unit set 1 is forming casein micelles in vivo in an embodiment. In this example, the plant transformation depicts a plant transformed using a T-DNA including four transcription unit sets shown and annotated in FIG. 3A as 4-TUS plasmid. The T-DNA includes transcription unit set 1, shown and abbreviated in FIG. 3A as $TUS_1$, which includes one transcription unit for each of the four casein proteins found in a casein micelle, with each transcription unit including DNA encoding the same plant-derived signal peptide, a promoter and a transcriptional terminator as described in FIG. 2. Upon transcription and translation of $TUS_1$ in the transgenic plant during the recombinant casein protein formation, the four recombinant casein proteins ($αS_1$-casein, $αS_2$-casein, $β$-casein, and $κ$-casein) are formed in the cytoplasm, each including a signal peptide that localizes the recombinant protein to a specific tissue, for example the secretory pathway and protein storage vacuoles, in the plant cell. In this example, the signal peptide is removed from the recombinant casein proteins during post-translational modification that occurs in the endoplasmic reticulum, abbreviated as ER, of the plant cell.

Continuing this example and embodiment for the post-translation modification, phosphorylation occurs on the recombinant casein proteins prior to, during, or after migration to a specific tissue. The phosphorylation is shown in FIG. 3A as circles enclosing the letter "P" that are added to and then attached to each of the recombinant casein proteins to form phosphorylated casein proteins. The phosphorylated casein proteins are then localized to the vacuole where micelle assembly occurs in vivo. In some embodiments, proteins encoded by $TUS_2$ transcription units (not shown) are also phosphorylated, glycosylated, or a combination thereof. In other embodiments, the casein proteins encoded by $TUS_4$ transcription units (not shown) are also phosphorylated or glycosylated or both. In other embodiments, no post-translational modifications occur to proteins encoded by TUS 1, $TUS_2$, $TUS_3$, or $TUS_4$ (not shown). As another example and embodiment, a kinase gene may optionally be included to generate a kinase protein that ensures phosphorylation of the casein proteins encoded by $TUS_4$ transcription units (not shown).

Figure 3B:
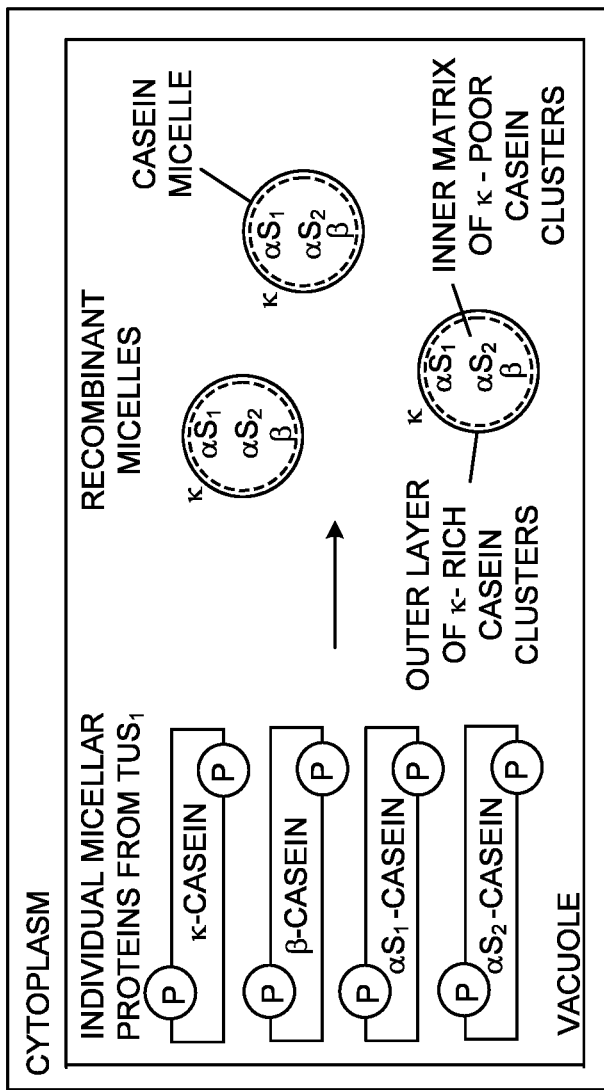
FIG. 3B is an example with additional details for the in vivo formation.

Referring now to FIG. 3B, therein is shown an example with additional details for the in vivo formation. The in vivo formation is also described in FIG. 1. As a specific example, FIG. 3B schematically illustrates the in vivo formation of recombinant micelles inside a plant cell.

Upon localization to the vacuole, each of the four recombinant casein proteins assemble with the other recombinant casein proteins to form micelles in vivo. In this example, the outer layer of the micelle is enriched in recombinant κ-casein shown and abbreviated in FIG. 3B as κ, and the inner matrix of the micelle includes recombinant $αS_1$-casein and $αS_2$-casein, shown and abbreviated as $αS_1$ and $αS_2$, respectively, in FIG. 3B, and β-casein, shown and abbreviated in FIG. 3B as β.

Figure 3C:
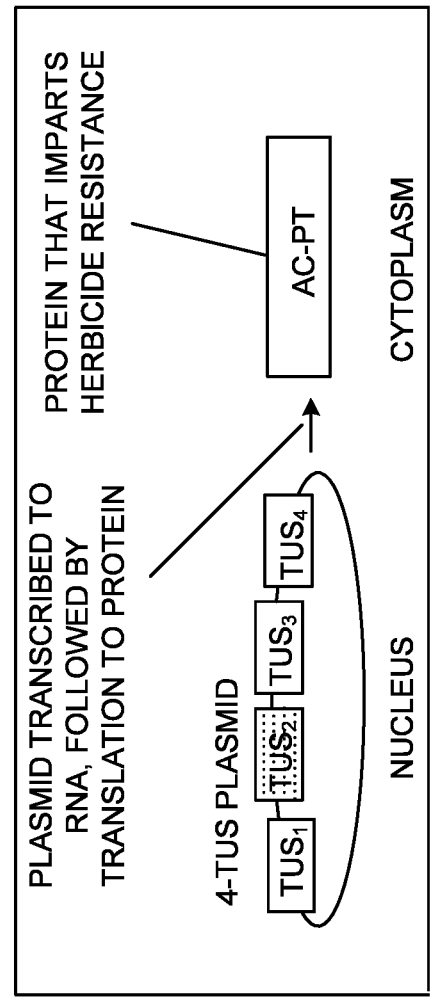
FIG. 3C is an example of a schematic illustration of a transcription of proteins which impart herbicide resistance to the transformed plant.

Referring now to FIG. 3C, therein is shown an example of a schematic illustration of a transcription of proteins which impart herbicide resistance to the transformed plant. FIG. 3C depicts an example of the purpose of transcription unit set 2 in an embodiment.

In this example, a plant is transformed using a T-DNA including four transcription unit sets shown and annotated in FIG. 3C as 4-TUS plasmid. The T-DNA includes transcription unit set 2, shown in FIG. 3C and abbreviated as $TUS_2$ which includes one transcription unit that includes DNA encoding phosphinothricin acetyltrasnferase that imparts herbicide resistance and allow for selection of transformed cells producing micelles, shown and abbreviated as AC-PT in FIG. 3C, and a promoter and a transcriptional terminator (not shown).

Figure 3E:
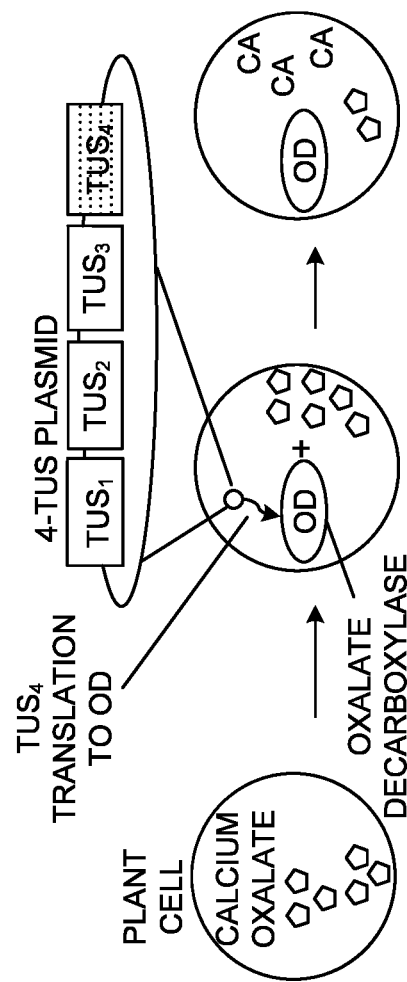
FIG. 3E is an example of a schematic illustration of a transcription of a portion of the plasmid of FIG. 1 and resulting proteins used to increase calcium concentrations in the plant cell.
Figure 3D:
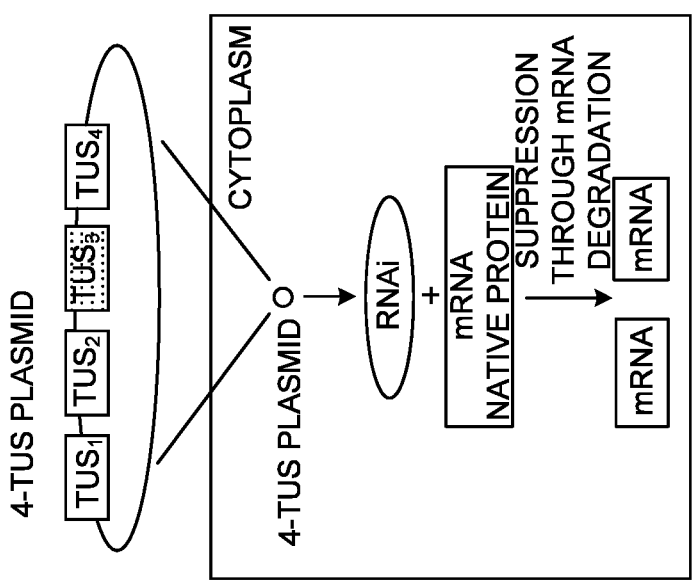
FIG. 3D is an example of a schematic illustration of suppression of native seed storage proteins by RNAi transcribed by a portion of the plasmid of FIG. 1.

Referring now to FIG. 3D, therein is shown an example of a schematic illustration of suppression of native seed storage proteins by interference RNA (RNAi) transcribed by a portion of the plasmid of FIG. 1. As a specific example, FIG. 3D schematically illustrates suppression of native seed storage proteins by RNAi transcribed by one or more genes in $TUS_3$.

FIG. 3D depicts an example of the purpose of transcription unit set 3 in an embodiment. In this example, a plant is transformed using a T-DNA including four transcription unit sets, shown and annotated in FIG. 3D as 4-TUS plasmid. The T-DNA includes transcription unit set 3, shown and abbreviated in FIG. 3D as TUS$_3$, which includes one or more transcription units that yield untranslated RNA molecules that suppress native seed protein gene translation thereby freeing cellular resources to produce micelles in vivo. Transcription of the DNA in TUS$_3$ yields RNAi, shown and abbreviated in FIG. 3D as RNAi, that targets messenger RNA of native plant proteins or native plant peptides, shown and annotated in FIG. 3D as mRNA NATIVE PROTEIN, and suppresses the expression of those messenger RNAs through messenger RNA degradation such that the recombinant casein proteins encoded by TUS$_1$, described in FIG. 1, FIG. 3A, and FIG. 3B, can be translated at higher quantities, thereby yielding higher concentrations of micelles in vivo (not shown). In some embodiments, DNA encoding RNAi is operably linked to a constitutive promoter or an inducible promoter (not shown), such as for example a nopaline synthase promoter or soybean α' subunit of β-conglycinin, such that the suppression of native seed protein gene translation by RNAi can be regulated.

Figure 3F:
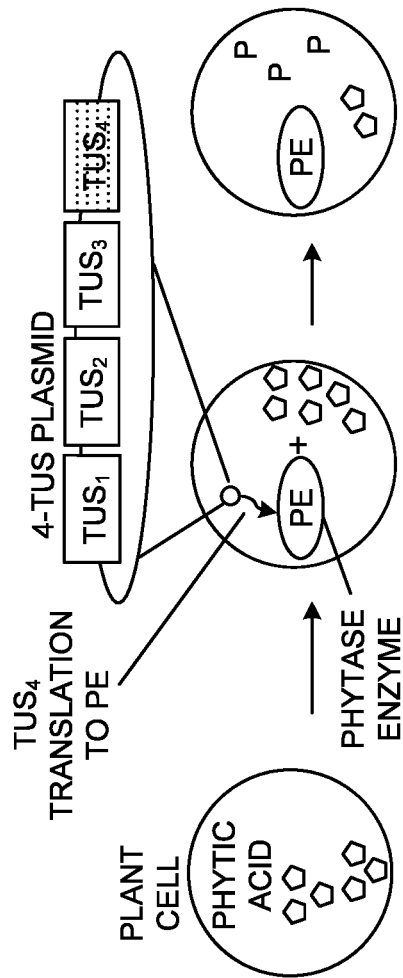
FIG. 3F is an example of a schematic illustration of a transcription of a portion of the plasmid of FIG. 1 and resulting proteins used to increase phosphate concentrations in the plant cell.

Referring now to FIG. 3E and FIG. 3F, therein are shown examples of schematic illustrations of a transcription of a portion of the plasmid of FIG. 1 and resulting proteins used to alter the intracellular conditions of the plant cell. As specific examples, FIG. 3E and FIG. 3F schematically illustrate the transcription of TUS$_4$ genes and the resulting proteins used to alter the conditions in the cytoplasm of the cell.

FIG. 3E depicts an example of the purpose of transcription unit set 4 in an embodiment. In this example, a plant is transformed using a T-DNA including four transcription unit sets, shown and annotated in FIG. 3E as 4-TUS plasmid. The T-DNA includes transcription unit set 4, shown and abbreviated in FIG. 3E as TUS$_4$, which includes one or more transcription units that encode proteins which increase the concentration of intracellular minerals, including calcium and phosphate. In this example, TUS$_4$ includes one transcription unit, a TU$_{4-1}$, that includes a promoter, DNA encoding oxalate decarboxylase, and a transcriptional terminator (not shown). Transcription and translation of TU$_{4-1}$ yields the enzyme oxalate decarboxylase, shown and abbreviated in FIG. 3E as OD, that breaks down the calcium oxalate and increases calcium levels in the plant cell. The increased intracellular calcium enhances the formation of recombinant casein micelles in the plant cell (not shown).

FIG. 3F depicts an example of the purpose of transcription unit set 4 in an embodiment. In this example, a plant is transformed using a T-DNA including four transcription unit sets, shown and annotated in FIG. 3F as 4-TUS plasmid. The T-DNA includes transcription unit set 4, shown and abbreviated in FIG. 3F as TUS$_4$, which includes one or more transcription units that encode proteins which increase the concentration of intracellular minerals, including calcium and phosphate. In this example, TUS$_4$ includes one transcription unit, a TU$_{4-2}$, that includes a promoter, DNA encoding a phytase enzyme, and a transcriptional terminator (not shown). Transcription and translation of TU$_{4-2}$ yields the phytase enzyme, shown and abbreviated in FIG. 3F as PE, that breaks down the phytic acid and increases phosphate levels in the plant cell. The increased intracellular phosphate enhances the formation of recombinant casein micelles in the plant cell (not shown).

Figure 3G:
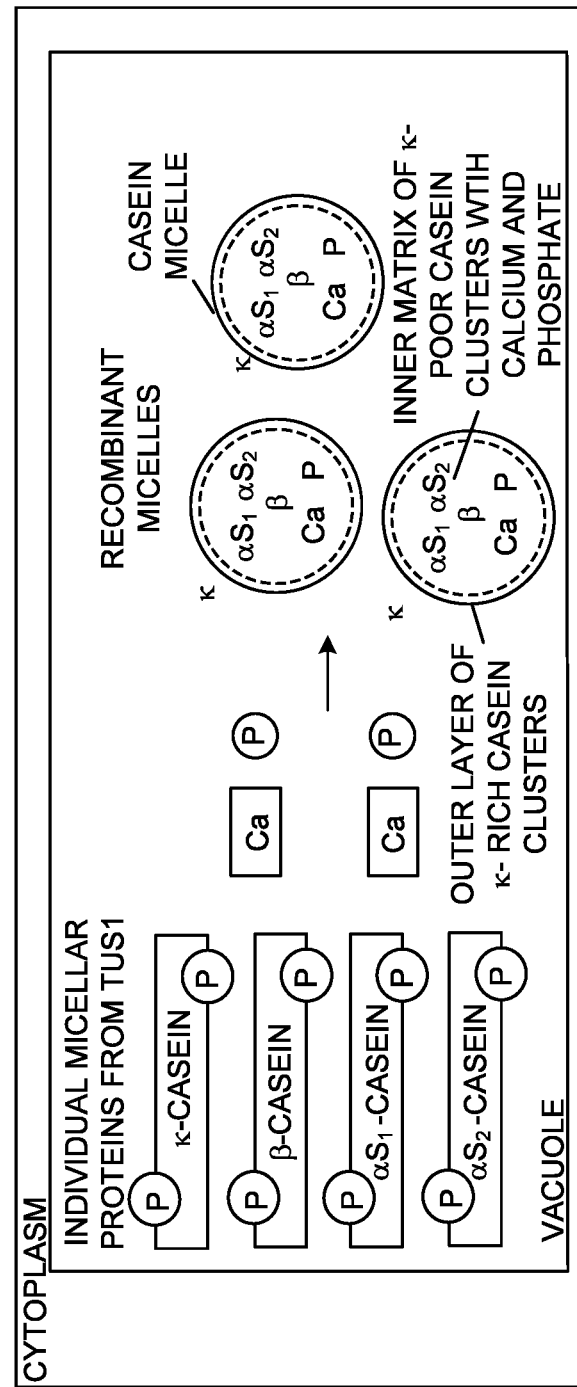
FIG. 3G is an example with further additional details of the in vivo formation.

Referring now to FIG. 3G, therein is shown an example of further additional details of the in vivo formation. The in vivo formation is also described in FIG. 1, FIG. 3A, and FIG. 3B. As a specific example, FIG. 3G schematically illustrates the in vivo formation of recombinant micelles inside a plant cell.

In the example shown in FIG. 3G, the in vivo formation of recombinant micelles inside a plant cell in which the four micellar proteins are produced by transcription and translation of transcription unit set 1 as depicted and described in FIG. 3A. The levels of calcium in plant cell vacuoles is increased by the presence of oxalate decarboxylase produced by transcription and translation of transcription unit set 4 as depicted and described in FIG. 3E. In this example, the four casein proteins encoded by transcription unit 1 are phosphorylated and localized to the plant cell vacuole where the intracellular calcium and the intracellular phosphate enhances the formation of recombinant casein micelles in the plant cell vacuole.

Figure 4:
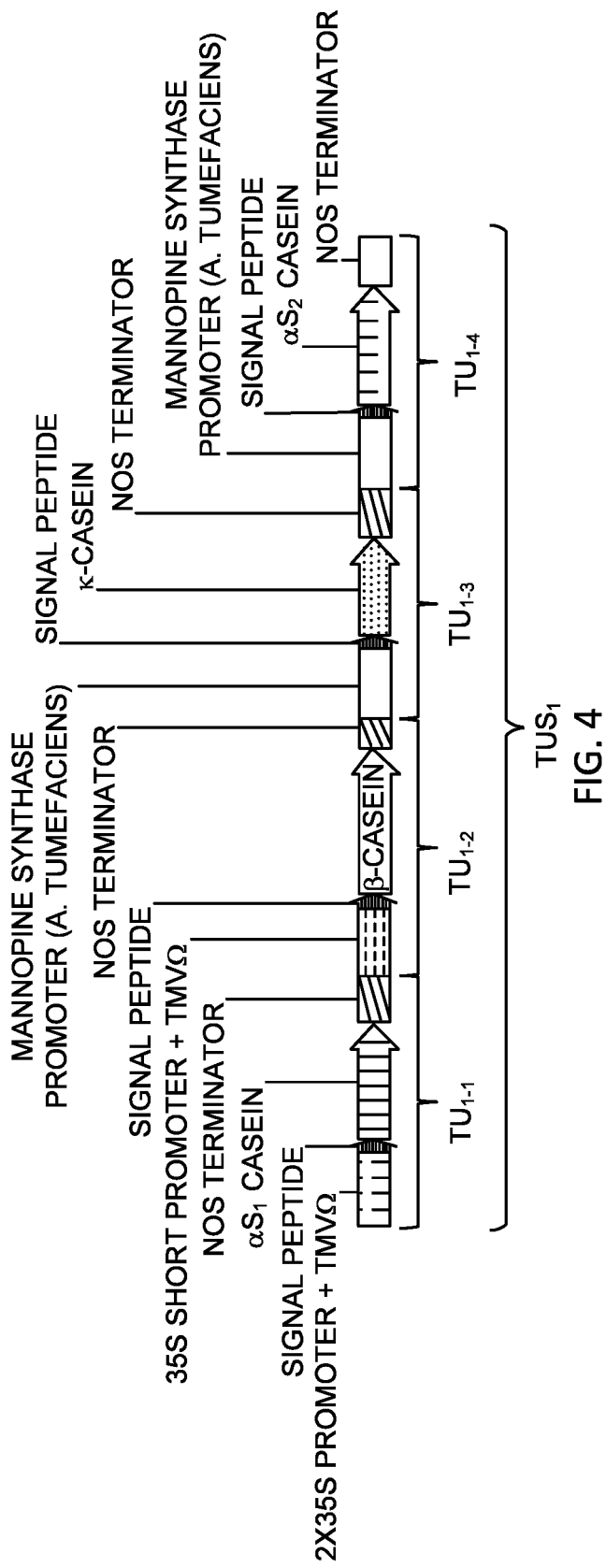
FIG. 4 is an example of a schematic illustration of a portion of a plasmid in *Arabidopsis*.
Figure 5:
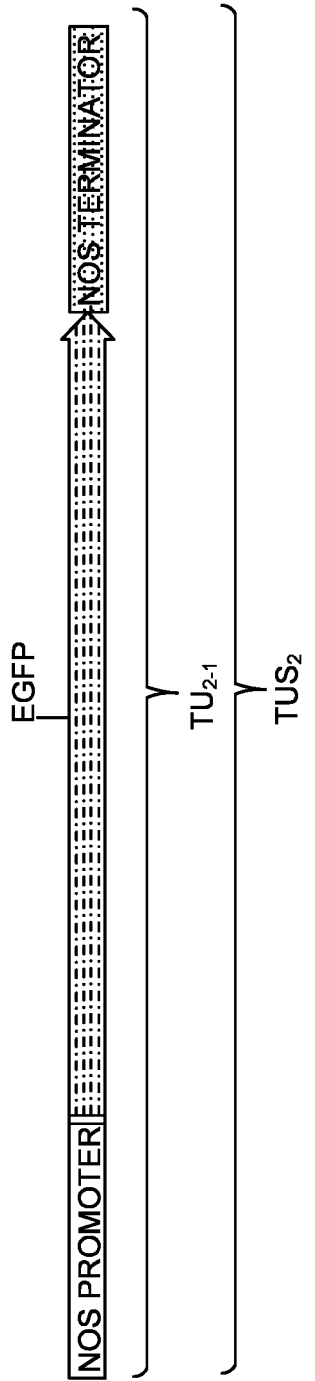
FIG. 5 is an example of a schematic illustration of a portion of a plasmid in *Arabidopsis* for a screenable marker in plants.

Aspects of the disclosure can be further illustrated by a specific embodiment in which a casein micelle is assembled in vivo from its constituent proteins in *Arabidopsis thaliana* as further described in FIG. 4 and FIG. 5.

Referring now to FIG. 4, therein is shown an example of a schematic illustration of a portion of a plasmid in *Arabidopsis*. The example shown in FIG. 4 is also described in FIG. 2. As a specific example, FIG. 4 schematically illustrates elements of plasmids that encode micellar component proteins. Transcription units depicted are components of TUS$_1$ in *Arabidopsis*.

The example in FIG. 4 depicts a transcription unit set which can be used for creation of casein micelles in vivo in *Arabidopsis thaliana*. The transcription unit set includes one transcription unit for each of the four casein proteins found in a casein micelle, abbreviated and shown in FIG. 4 as TU$_{1-1}$, TU$_{1-2}$, TU$_{1-3}$, and TU$_{1-4}$. The transcription unit set abbreviated and shown in FIG. 4 as TUS$_1$. Each of the four transcription units includes a promoter, a plant-derived N-terminal signal peptide, DNA encoding one of the four proteins found in a casein micelle, and a transcriptional terminator.

Continuing this example, TU$_{1-1}$ includes a double 35S promoter containing the tobacco mosaic virus omega leader sequence (SEQ ID NO:29), a signal peptide from the *Arabidopsis* CLV3 gene (SEQ ID NO:27), the αS$_1$-casein coding sequence codon optimized for expression in *Arabidopsis* with a C-terminal HDEL peptide for retention in the endoplasmic reticulum (SEQ ID NO:5), and the nopaline synthase terminator (SEQ ID NO:35), annotated and shown in FIG. 4 as 2X35S promoter+TMVΩ, signal peptide, αS$_1$ casein, and NOS terminator, respectively.

Further continuing this example, TU$_{1-2}$ includes a 35S short promoter containing a truncated version of the cauliflower mosaic virus promoter and the tobacco mosaic virus omega leader sequence (SEQ ID NO:31), a signal peptide (SEQ ID NO:27), the β-casein coding sequence codon optimized for expression in *Arabidopsis* with a C-terminal HDEL peptide for retention in the endoplasmic reticulum (SEQ ID NO:7), and the nopaline synthase terminator (SEQ ID NO:35), abbreviated and shown in FIG. 4 as 35S SHORT PROMOTER+TMVΩ, SIGNAL PEPTIDE, β-CASEIN, and NOS TERMINATOR, respectively.

Further continuing this example, TU$_{1-3}$ includes the mannopine synthase promoter from *Agrobacterium tumefaciens* (SEQ ID NO:32), a signal peptide (SEQ ID NO:27), the κ-casein coding sequence codon optimized for expression in *Arabidopsis* with a C-terminal HDEL peptide for retention in the endoplasmic reticulum (SEQ ID NO:6), and the nopaline synthase terminator (SEQ ID NO:35), abbreviated and shown in FIG. 4 as MANNOPINE SYNTHASE PROMOTER (*A. Tumefaciens*), SIGNAL PEPTIDE, κ-CASEIN, and NOS TERMINATOR, respectively.

Further continuing this example, $TU_{1-4}$ includes the mannopine synthase promoter from *Agrobacterium tumefaciens*, a signal peptide (SEQ ID NO:32), the $\alpha S_2$-casein coding sequence codon optimized for expression in *Arabidopsis* with a C-terminal HDEL peptide for retention in the endoplasmic reticulum (SEQ ID NO:8), and the nopaline synthase terminator (SEQ ID NO:35), abbreviated and shown in FIG. 4 as MANNOPINE SYNTHASE PROMOTER (*A. Tumefaciens*), SIGNAL PEPTIDE, $\alpha S_2$ CASEIN, and NOS TERMINATOR, respectively.

Referring now to FIG. 5, therein is shown an example of a schematic illustration of a portion of a plasmid in *Arabidopsis* for a screenable marker in plants. As a specific example, FIG. 5 schematically illustrates elements of plasmids that provide for a screenable marker in plants. Transcription units depicted are components of $TUS_2$ in *Arabidopsis*.

The example shown in FIG. 5 depicts a transcription unit set which can be used to identify plant cells that have been transformed. The transcription unit set, abbreviated and shown in FIG. 5 as $TUS_2$, includes a single transcription unit, abbreviated and shown in FIG. 5 as $TU_{2-1}$.

Continuing this example for a portion of the plant transformation shown in FIG. 5 as an embodiment, $TU_{2-1}$ includes the nopaline synthase constitutive promoter (SEQ ID NO:28), the enhanced green fluorescence protein coding sequence modified to enhance fluorescence brightness and codon optimized for expression in *Arabidopsis* (SEQ ID NO:33), and the nopaline synthase terminator (SEQ ID NO:35), abbreviated and shown in FIG. 5 as NOS PROMOTER, EGFP, and NOS TERMINATOR, respectively.

As a specific example, subsequent steps in the plant transformation for creation of casein micelles in vivo in *Arabidopsis thaliana*, a plasmid including $TUS_1$ and $TUS_2$ can be introduced into *Arabidopsis thaliana* cotyledons using *Agrobacterium tumefaciens* and the FAST transient expression method. Seedlings are soaked in a solution containing *Agrobacterium* two days after germination which results in some cotyledon cells being transformed. Transformed *Arabidopsis* cells can be identified as containing the T-DNA by observing fluorescence exhibited by the enhanced green fluorescence protein. Successfully transformed *Arabidopsis* cells display green fluorescence while unsuccessfully transformed cells show little or no green fluorescence.

Also as a specific example of the in vivo formation of micelles in *Arabidopsis thaliana* as an embodiment, immunogold labeling techniques can be used to identify the location and morphology of the casein micelles formed in vivo. For this example for the in vivo formation of micelles as an embodiment, embryonic tissue can be obtained from *Arabidopsis thaliana* that has been transformed with a plasmid including TUS 1, and optionally $TUS_2$, shown in FIG. 4 and FIG. 5, respectively. The embryonic tissue can be treated with casein-specific antibodies using immunogold labeling techniques, and imaged with transmission electron microscopy to identify the location and morphology of the micelles formed in vivo. In tissue obtained from the transformed *Arabidopsis thaliana*, the casein micelles are visualized as gold-antibody labeled subcellular structures that range in size from 50 nm to 600 nm, which is similar to the size of bovine casein micelles. As a control, no casein micelles are visualized using immunogold labeling techniques in tissue obtained from untransformed *Arabidopsis thaliana*.

Continuing this specific example of the in vivo formation of micelles in *Arabidopsis thaliana* as an embodiment, protein extraction and high performance liquid chromatography (HPLC) analysis can be used to evaluate the protein composition of the casein micelles formed in vivo. In this example for the in vivo formation of micelles as an embodiment, embryonic tissue can be obtained from *Arabidopsis thaliana* that has been transformed with a plasmid including $TUS_1$, and optionally $TUS_2$, shown in FIG. 4 and FIG. 5, respectively. Proteins extracted from the embryonic tissue can be separated using HPLC and detected by ultraviolet absorbance. Proteins extracted from the transformed *Arabidopsis thaliana* tissue and subjected to HPLC analysis show peaks associated with each four proteins found in a casein micelle, including $\alpha S_1$ casein, $\alpha S_2$ casein, $\beta$ casein, and $\kappa$ casein, that display retention times similar to those reported by Bordin et al. for each of the four casein proteins found in bovine casein micelles. As a control, proteins extracted from the untransformed *Arabidopsis thaliana* tissue and subjected to HPLC analysis do not show peaks associated with any of the four casein proteins.

Further continuing this specific example of the in vivo formation of micelles in *Arabidopsis thaliana* as an embodiment, the amount of each casein protein found in micelles formed in vivo can be quantified by measuring the area under the peaks produced upon HPLC analysis. Quantification of the peaks produced upon HPLC analysis of proteins extracted from transformed *Arabidopsis thaliana* produces measurements showing that $\alpha S_1$ casein is the most abundant, followed by $\beta$ casein as the next most abundant, then $\alpha S_2$ casein and $\kappa$ casein as the least abundant casein proteins, which correlates to the relative abundances of each of the four casein proteins in bovine casein micelles as previously reported in the Handbook of Dairy Foods and Nutrition, Table 1.1.

Aspects of the disclosure can be further illustrated by a specific embodiment in which a casein micelle is assembled in vivo from its constituent proteins in soybean and further described in FIG. 6 through FIG. 9.

Referring now to FIG. 6, therein is shown an example of a schematic illustration of a portion of a plasmid in soybean. As a specific example, FIG. 6 schematically illustrates elements of plasmids that encode micellar component proteins. Transcription units depicted are components of $TUS_1$ in soybean.

In this example, FIG. 6 depicts a transcription unit set which can be used for creation of casein micelles in vivo in soybean. The transcription unit set includes one transcription unit for each of the four casein proteins found in a casein micelle, abbreviated and shown in FIG. 4 as $TU_{1-1}$, $TU_{1-2}$, $TU_{1-3}$, and $TU_{1-4}$. The first transcription unit set is abbreviated and shown in FIG. 6 as TUS 1. Each of the four transcription units includes a promoter, a plant-derived N-terminal signal peptide, DNA encoding one of the four proteins found in a casein micelle, and a transcriptional terminator.

Continuing this example for a portion of the plant transformation shown in FIG. 6 as an embodiment, $TU_{1-1}$ includes a promoter from the soybean glycinin GY1 gene (SEQ ID NO:13), a signal peptide (SEQ ID NO:26), the $\alpha S_1$ casein coding sequence codon optimized for expression in soybean (SEQ ID NO:1), and the nopaline synthase terminator (SEQ ID NO:35), abbreviated and shown in FIG. 6 as GY1 PROMOTER, SIGNAL PEPTIDE, $\alpha S_1$ CASEIN, and NOS TERMINATOR, respectively.

Further continuing this example for a portion of the plant transformation shown in FIG. 6 as an embodiment, $TU_{1-2}$ includes the promoter from the soybean CG1 gene (SEQ ID NO:14), a signal peptide (SEQ ID NO:26), the $\beta$ casein coding sequence codon optimized for expression in soybean (SEQ ID NO:3), and the nopaline synthase terminator (SEQ ID NO:35), abbreviated and shown in FIG. 6 as CG1 PROMOTER, SIGNAL PEPTIDE, β CASEIN, and NOS TERMINATOR, respectively.

Further continuing this example for a portion of the plant transformation shown in FIG. 6 as an embodiment, $TU_{1-3}$ includes the promoter from the soybean glycinin GY4 gene (SEQ ID NO:15), a signal peptide (SEQ ID NO:26), the κ casein coding sequence codon optimized for expression in soybean (SEQ ID NO:2), and the nopaline synthase terminator (SEQ ID NO:35), abbreviated and shown in FIG. 6 as GY4 PROMOTER, SIGNAL PEPTIDE, κ CASEIN, and NOS TERMINATOR, respectively.

Further continuing this example for a portion of the plant transformation shown in FIG. 6 as an embodiment, $TU_{1-4}$ includes the promoter from the soybean D-II Bowman-Birk proteinase isoinhibitor gene (SEQ ID NO:16), a signal peptide (SEQ ID NO:26), the 1362 casein coding sequence codon optimized for expression in soybean (SEQ ID NO:4), and the nopaline synthase terminator (SEQ ID NO:35), abbreviated and shown in FIG. 6 as D-II PROMOTER, SIGNAL PEPTIDE, $αS_2$ CASEIN, and NOS TERMINATOR, respectively.

Referring now to FIG. 7, therein is shown an example of a schematic illustration of a portion of a plasmid in soybean for herbicide resistance in plants. As a specific example, FIG. 7 schematically illustrates elements of plasmids that provide for herbicide resistance in plants. Transcription units depicted are components of $TUS_2$ in soybean.

FIG. 7 is an example of a portion of the plant transformation that depicts a transcription unit set which can be used to select for plant cells that have been transformed. The transcription unit set abbreviated and shown in FIG. 7 as $TUS_2$ includes a single transcription unit abbreviated and shown in FIG. 7 as $TU_{2-1}$.

Continuing this example for a portion of the plant transformation shown in FIG. 7 as an embodiment, $TU_{2-1}$ includes nopaline synthase promoter (SEQ ID NO:28), the phosphinothricin acetyltransferase coding sequence codon optimized for expression in soybean (SEQ ID NO:34) which confers resistance to the herbicide glufosinate, and the nopaline synthase terminator (SEQ ID NO:35), abbreviated and shown in FIG. 7 as NOS PROMOTER, PHOSPHINOTHRICIN ACETYLTRANSFERASE, and NOS TERMINATOR, respectively.

Figure 8:
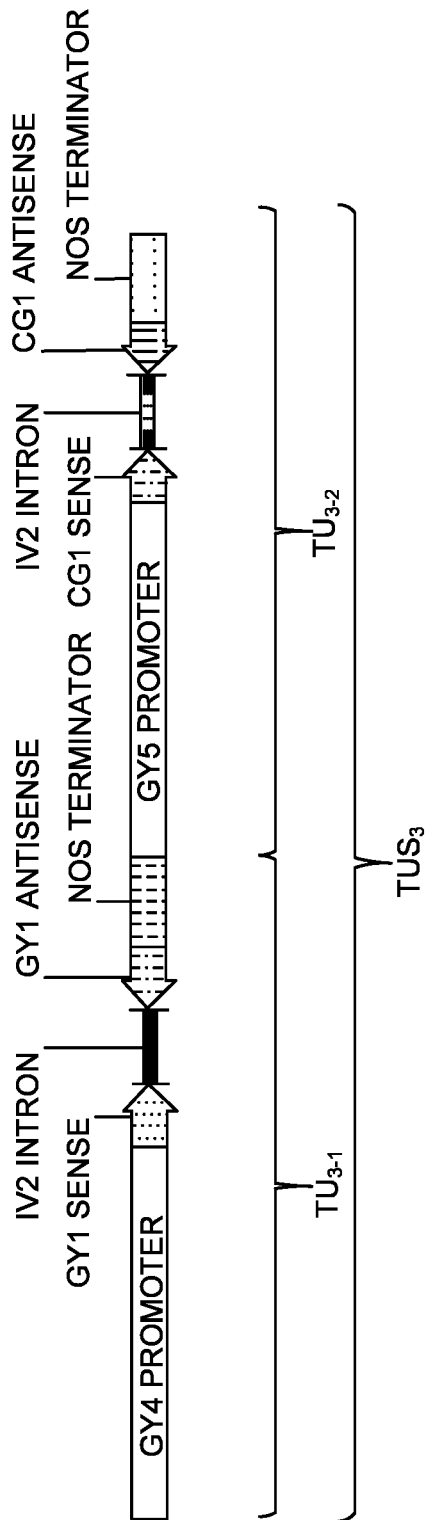
FIG. 8 is an example of a schematic illustration of a portion of the plasmid of FIG. 1 for soybean for suppression of native seed storage proteins in plants.

Referring now to FIG. 8, therein is shown an example of a schematic illustration of a portion of a plasmid in soybean for suppression of native seed storage proteins in plants. As a specific example, FIG. 8 schematically illustrates elements of plasmids that provide for suppression of native seed storage proteins in plants. Transcription units depicted are components of $TUS_3$ in soybean.

FIG. 8 is an example of a portion of the plant transformation that depicts a transcription unit set which can be used for enhancing the creation of casein micelles in vivo in soybean. The third transcription unit set abbreviated and shown in FIG. 8 as $TUS_3$ includes two transcription units abbreviated and shown in FIG. 8 as $TU_{3-1}$ and $TU_{3-2}$. The transcription of $TU_{3-1}$ and $TU_{3-2}$ produces RNA with a hairpin structure where the arms are homologous to a portion of a native soybean gene or gene family and are sufficient to cause down regulation of those native genes or gene families (not shown).

Continuing this example for a portion of the plant transformation shown in FIG. 8 as an embodiment, $TU_{3-1}$ includes a promoter from the soybean glycinin GY4 gene (SEQ ID NO:15), a portion of the soybean glycinin GY1 coding sequence that is lacking a start codon and is highly homologous among the glycinin gene family (SEQ ID NO:24), the potato IV2 intron (SEQ ID NO:25), the antisense of the soybean glycinin GY1 sequence (SEQ ID NO:17), and the nopaline synthase terminator (SEQ ID NO:35), abbreviated and shown in FIG. 8 as GY4 PROMOTER, GY1 SENSE, IV2 INTRON, GY1 ANTISENSE, and NOS TERMINATOR, respectively.

Further continuing this example for a portion of the plant transformation shown in FIG. 8 as an embodiment, $TU_{3-2}$ includes a promoter from the soybean glycinin GY5 gene (SEQ ID NO:18), a portion of the soybean β-conglycinin 1 coding sequence that is lacking a start codon and is highly homologous among the β-conglycinin gene family (SEQ ID NO:19), the potato IV2 intron (SEQ ID NO:25), the antisense of the soybean β-conglycinin 1 sequence (SEQ ID NO:20), and the nopaline synthase terminator (SEQ ID NO:35), abbreviated and shown in FIG. 8 as GY5 PROMOTER, CG1 SENSE, IV2 INTRON, CG1 ANTISENSE, and NOS TERMINATOR, respectively.

Figure 9:
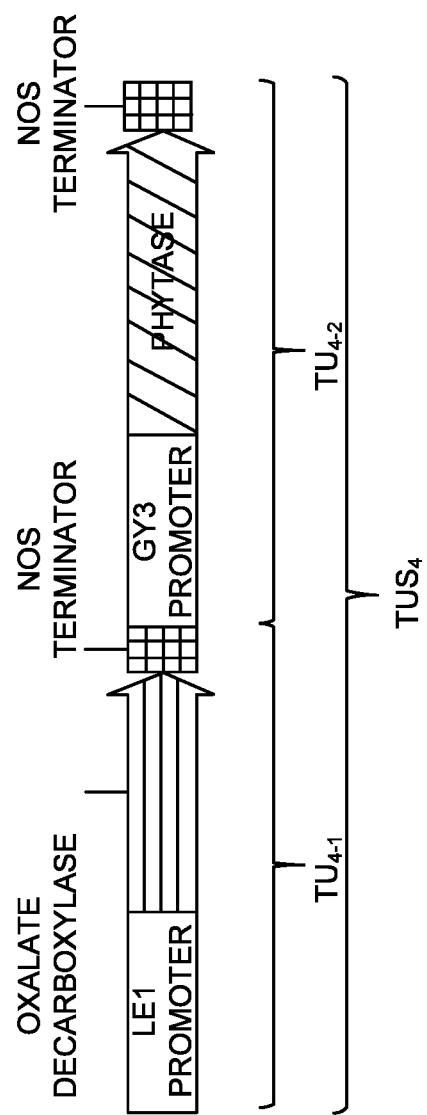
FIG. 9 is an example of a schematic illustration of a portion of a plasmid for soybean to regulate intracellular concentrations of minerals which can enhance micelle formation.

Referring now to FIG. 9, therein is shown an example of a schematic illustration of a portion of a plasmid in soybean for regulating cytoplasmic concentrations of minerals which can enhance micelle formation. As a specific example, FIG. 9 schematically illustrates elements of plasmids that regulate cytoplasmic concentrations of minerals which can enhance micelle formation. Transcription units depicted are components of $TUS_4$ in soybean.

FIG. 9 is an example of a portion of the plant transformation that depicts a transcription unit set which can be used for enhancing the creation of casein micelles in vivo in soybean. The fourth transcription unit set abbreviated and shown in FIG. 9 as $TUS_4$ includes two transcription units abbreviated and shown in FIG. 9 as $TU_{4-1}$ and $TU_{4-2}$. Proteins encoded by $TU_{4-1}$ and $TU_{4-2}$ alter the intracellular environment in a manner that optimizes the formation of micelles in vivo.

Continuing this example for a portion of the plant transformation shown in FIG. 9 as an embodiment, $TU_{4-1}$ includes a promoter from the soybean LE1 gene (SEQ ID NO:23), a coding sequence for oxalate decarboxylase from *Flammulina velutipes* codon optimized for expression in soybean (SEQ ID NO:12), and nopaline synthase terminator (SEQ ID NO:35), abbreviated and shown in FIG. 9 as LE1 PROMOTER, OXALATE DECARBOXYLASE CDS, and NOS TERMINATOR, respectively.

Further continuing this example for a portion of the plant transformation shown in FIG. 9 as an embodiment, $TU_{4-2}$ includes the glycinin GY3 promoter (SEQ ID NO:30), the coding sequence for a soybean phytase enzyme (SEQ ID NO:11), and the nopaline synthase terminator (SEQ ID NO:35), abbreviated and shown in FIG. 9 as GY3 PROMOTER, PHYTASE, and NOS TERMINATOR, respectively.

In this example, subsequent steps in the plant transformation for creation of casein micelles in vivo in soybean, a plasmid including $TUS_1$, $TUS_2$, and optionally $TUS_3$, and optionally $TUS_4$, shown in FIG. 6, FIG. 7, FIG. 8, and FIG. 9, respectively, can be introduced into soybean callus using standard biolistic transformation methods. Transformed soybean plants can be selected on a medium containing glufosinate herbicide, and the genomes of transformed soybean plants can be screened for insertion of the plasmid using standard PCR mapping methods. Transformed soybean plants including $TUS_1$, $TUS_2$, and optionally $TUS_3$, and optionally $TUS_4$ in their genome can be transferred to a greenhouse for seed production.

In the example of the in vivo formation of micelles in soybean as an embodiment, immunogold labeling techniques can be used to identify the location and morphology of the casein micelles formed in vivo. As it relates to this example for the in vivo formation of micelles as an embodiment, tissue can be obtained from soybean plants that have been transformed with a plasmid including $TUS_1$, $TUS_2$, and optionally $TUS_3$, and optionally $TUS_4$, shown in FIG. 6, FIG. 7, FIG. 8, and FIG. 9, respectively. The tissue can be treated with casein-specific antibodies using standard immunogold labeling techniques, and imaged with transmission electron microscopy to identify the location and morphology of the micelles formed in vivo. In tissue obtained from the transformed soybean plants, the casein micelles are visualized as gold-antibody labeled subcellular structures that range in size from 50 nm to 600 nm, which is similar to the size of bovine casein micelles. As a control, no casein micelles are visualized using immunogold labeling techniques in tissue obtained from untransformed soybean plants.

Continuing this example of the in vivo formation of micelles in soybean as an embodiment, protein extraction and polyacrylamide gel electrophoresis analysis can be used to evaluate the protein composition of the casein micelles formed in vivo. For this example for the in vivo formation of micelles as an embodiment, tissue can be obtained from soybean plants that have been transformed with a plasmid including $TUS_1$, $TUS_2$, and optionally $TUS_3$, and optionally $TUS_4$, shown in FIG. 6, FIG. 7, FIG. 8, and FIG. 9, respectively. Proteins extracted from the transformed soybean plant tissue and subjected to polyacrylamide gel electrophoresis analysis show bands on the polyacrylamide gel corresponding in size to each of the four casein proteins found in a casein micelle, including $\alpha S_1$ casein, $\alpha S_2$ casein, 13 casein, and κ casein. As a control, proteins extracted from untransformed soybean plant tissue and subjected to polyacrylamide gel electrophoresis analysis do not show bands on the polyacrylamide gel corresponding to the four casein proteins.

Further continuing this example of the in vivo formation of micelles in soybean as an embodiment, protein extraction and HPLC analysis can be used to evaluate the protein composition of the casein micelles formed in vivo. For this example for the in vivo formation of micelles as an embodiment, tissue can be obtained from soybean plants that have been transformed with a plasmid including $TUS_1$, $TUS_2$, and optionally $TUS_3$, and optionally $TUS_4$, shown in FIG. 6, FIG. 7, FIG. 8, and FIG. 9, respectively. Proteins extracted from the transformed soybean plant tissue can be separated using HPLC and detected by ultraviolet absorbance. Proteins extracted from the transformed soybean plant tissue and subjected to HPLC analysis show peaks associated with each four proteins found in a casein micelle, including $\alpha S_1$ casein, $\alpha S_2$ casein, β casein, and κ casein, that display retention times similar to those reported by Bordin et al. for each of the four casein proteins found in bovine casein micelles. As a control, proteins extracted from the untransformed soybean plant tissue and subjected to HPLC analysis do not show peaks associated with the four casein proteins.

Further continuing this example of the in vivo formation of micelles in soybean as an embodiment, the amount of each casein protein found in micelles formed in vivo can be quantified by measuring the area under the peaks produced upon HPLC analysis. Quantification of the peaks produced upon HPLC analysis of proteins extracted from transformed soybean plant tissue produces measurements showing that $\alpha S_1$ casein is the most abundant, followed by β casein as the next most abundant, then $\alpha S_2$ casein and κ casein as the least abundant casein proteins, which correlates to the relative abundances of each of the four casein proteins in bovine casein micelles as previously reported in the Handbook of Dairy Foods and Nutrition, Table 1.1.

Further continuing this example of the in vivo formation of micelles in soybean as an embodiment, RNA analysis can be used to evaluate the suppression of native soybean seed genes during the formation of casein micelles in vivo. For this example for the in vivo formation of micelles as an embodiment, soybean plants that have been transformed with a plasmid including $TUS_1$, $TUS_2$, $TUS_3$, and optionally $TUS_4$, shown in FIG. 6, FIG. 7, FIG. 8, and FIG. 9, respectively, can be grown to the flowering stage in a greenhouse and soybean embryos removed from the flowering seed pods at 35 days using standard dissection techniques. The expression levels of native soybean seed genes can be analyzed using standard techniques for RNA extraction and sequencing. RNA analysis of the embryos from transformed soybean plants show at least a 10% reduction in the expression of one or more of the native soybean seed genes, including genes in the glycinin family (Glyma.03g163500, Glyma.19g164900, Glyma.10g037100, Glyma.13g123500, Glyma.19g164800) and genes in the β-conglycinin family (Glyma.10g246300, Glyma.20g148400, Glyma.20g148300, Glyma.20g146200, Glyma.20g148200, Glyma.10g246500, Glyma.10g028300, Glyma.02g145700). As a control, RNA analysis of embryos from untransformed soybean plants do not show a reduction in the expression of native soybean seed genes.

Further continuing this example of the in vivo formation of micelles in soybean as an embodiment, commercially available assays and X-ray fluorescence techniques can be used to evaluate calcium oxalate levels during the formation of casein micelles in vivo. As it relates to this example for the in vivo formation of micelles as an embodiment, soybean plants that have been transformed with a plasmid including $TUS_1$, $TUS_2$, and optionally $TUS_3$, and $TUS_4$, shown in FIG. 6, FIG. 7, FIG. 8, and FIG. 9, respectively, can be grown to the flowering stage in a greenhouse and soybean embryos removed from the flowering seed pods at 27 days using standard dissection techniques. The oxalate concentration can be measured using commercially available assays, and the calcium concentration can be measured using X-ray fluorescence. Embryos from transformed soybean plants show at least a 5% reduction in oxalate concentration and at least a 4% increase in calcium concentration as compared to control embryos from untransformed soybean plants, indicating that embryos from transformed soybean plants have at least 4% more available calcium compared to embryos from untransformed soybean plants.

Further continuing this example of the in vivo formation of micelles in soybean as an embodiment, commercially available assays can be used to evaluate phosphate levels during the formation of casein micelles in vivo. As it relates to this example for the in vivo formation of micelles as an embodiment, soybean plants that have been transformed with a plasmid including $TUS_1$, $TUS_2$, and optionally $TUS_3$, and $TUS_4$, shown in FIG. 6, FIG. 7, FIG. 8, and FIG. 9., respectively, can be grown to the flowering stage in a greenhouse and soybean embryos removed from the flowering seed pods at 27 days using standard dissection techniques. Embryos can be ground with a mortar and pestle, sonicated and centrifuged to produce a supernatant that can be tested for phosphatase levels using commercially available assays. Embryos from transformed soybean plants show at least a 5% increase in phosphatase levels as compared to control embryos from untransformed soybean plants, indicating that embryos from transformed soybean plants have at least 5% more available phosphate compared to embryos from untransformed soybean plants.

Figure 10:
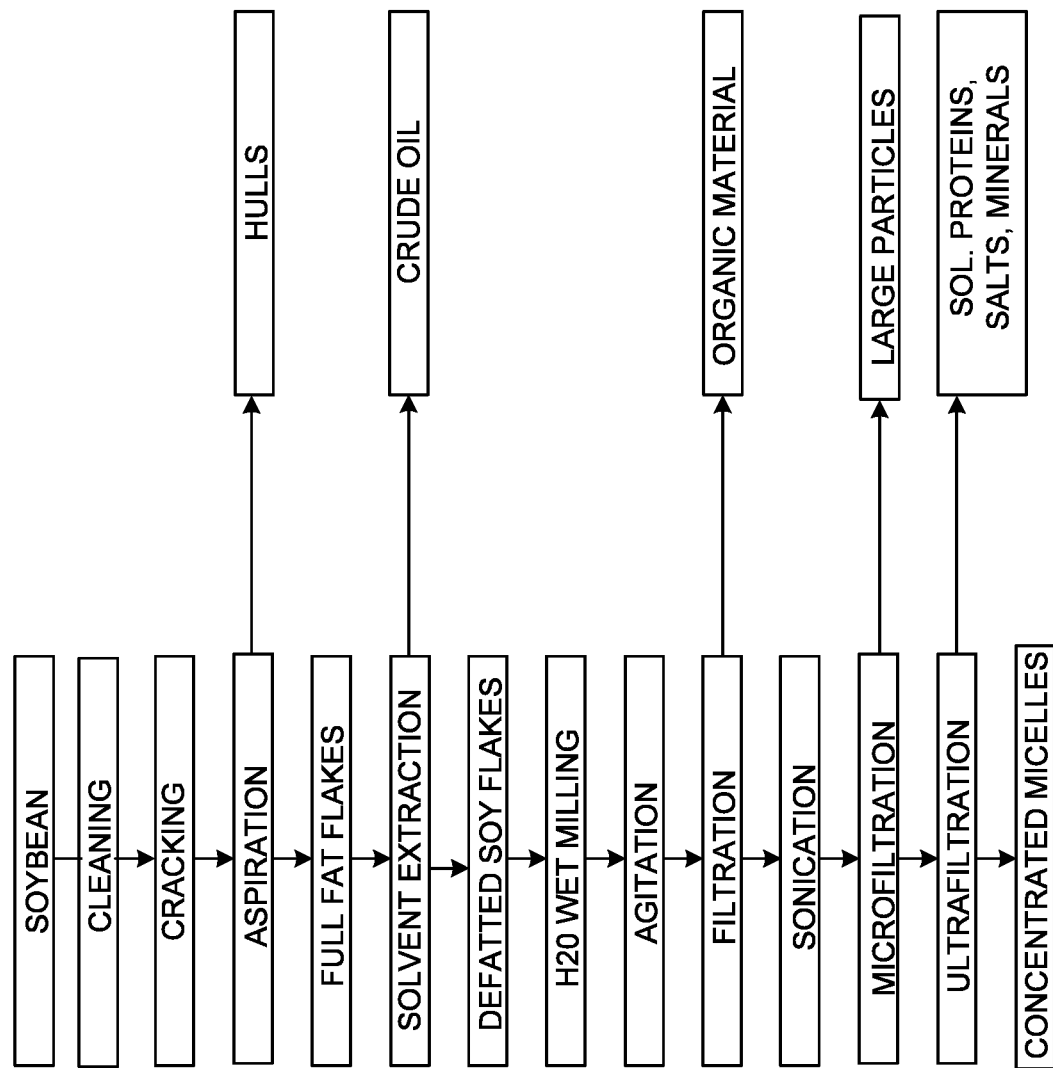
FIG. 10 is an example of a flow for the purification of micelles formed in vivo in soybean.

Aspects of the disclosure can be further illustrated by a specific embodiment in which micelles produced in vivo are purified as further described in FIG. 10.

Referring now to FIG. 10, therein is shown an example of a flow for the purification of micelles formed in vivo in soybean. Also, the flow in FIG. 10 is an example of isolating a recombinant micelle. Further in this example, FIG. 10 depicts a process where casein micelles produced in soybeans are purified from the plant tissue in a way that the micelles are still functional after the purification. The input material for the purification process is dried soybeans harvested from plants that have been transformed with a plasmid containing all four transcription unit sets, $TUS_1$, $TUS_2$, $TUS_3$, and $TUS_4$, described in FIG. 6, FIG. 7, FIG. 8, and FIG. 9, respectively. The input material for the purification process is shown in FIG. 10 and depicted as a rectangle enclosing the word "SOYBEAN".

Continuing this example of the purification of micelles formed in vivo in soybean as an embodiment, the hulls are removed from the dried soybeans in a series of steps including cleaning, cracking, and aspiration, shown in FIG. 10 and depicted as rectangles enclosing the words "CLEANING", "CRACKING" and "ASPIRATION". In this embodiment, the hulls do not contain useful amounts of casein micelles and are discarded, shown in FIG. 10 and depicted as an arrow pointing to a rectangle enclosing the word "HULLS".

Further continuing this example of the purification of micelles formed in vivo in soybean as an embodiment, the remaining material is flaked to increase the surface area and allow for faster aqueous or solvent infiltrations. The resulting flaked material is shown in FIG. 10 and depicted as a rectangle enclosing the words "FULL FAT FLAKES".

Further continuing this example of the purification of micelles formed in vivo in soybean as an embodiment, the flaked material is then defatted with hexane using standard defatting equipment and solvent extraction techniques, shown in FIG. 10 and depicted as a rectangle enclosing the words "SOLVENT EXTRACTION". Defatting can occur using any standard hexane based solvent, followed by desolventizing using flash or vapor-based processes. The resulting oil is removed, shown in FIG. 10 and depicted as an arrow pointing to a rectangle enclosing the words "CRUDE OIL", leaving behind the defatted flakes, shown in FIG. 10 and depicted as an arrow pointing to a rectangle enclosing the words "DEFATTED SOY FLAKES".

Further continuing this example of the purification of micelles formed in vivo in soybean as an embodiment, the defatted flakes are then mixed with water and wet milled, shown in FIG. 10 and depicted as an arrow pointing to a rectangle enclosing the words "H2O WET MILLING". The milling process pulverizes the defatted flakes which releases the casein micelles and allows the micelles to come into contact with an aqueous medium. In addition to the milling process, the defatted flakes are also vigorously agitated to assist in the release of casein micelles into the water, shown in FIG. 10 and depicted as an arrow pointing to a rectangle enclosing the word "AGITATION". The milling process and vigorous agitation of the defatted flakes yields a slurry where soybean material has been finely ground and many of the casein micelles have been released into suspension in the water (not shown). Additionally, many other proteins and carbohydrates are also dissolved in the water (not shown). In some embodiments, wet milling is done using perforated disc or colloid continuous flow mills.

Further continuing this example of the purification of micelles formed in vivo in soybean as an embodiment, the slurry is fed through a series of mesh screens to remove larger particles from the casein micelles, shown in FIG. 10 and depicted as an arrow pointing to a rectangle enclosing the word "FILTRATION". In this embodiment, the slurry is first passed through a screen with 5 mm sieve openings (not shown), and then is passed through a screen with 0.5 mm sieve openings (not shown). The material trapped by the screens is discarded, shown in FIG. 10 and depicted as an arrow pointing to a rectangle enclosing the words "ORGANIC MATERIAL".

Further continuing this example of the purification of micelles formed in vivo in soybean as an embodiment, the remaining material in the slurry that passed through both screens is then sonicated to break up aggregates of casein micelles such that the majority of micelles are not contacting other micelles, shown in FIG. 10 and depicted as an arrow pointing to a rectangle enclosing the word "SONICATION". In some embodiments, continuous flow sonication with multiple sonicators in parallel are used to maximize flow rates.

Further continuing this example of the purification of micelles formed in vivo in soybean as an embodiment, after sonication the slurry is passed through a 2 µm microfiltration unit to eliminate larger particles while allowing casein micelles to pass through, shown in FIG. 10 and depicted as an arrow pointing to a rectangle enclosing the word "MICROFILTRATION". The material trapped by the microfiltration unit is discarded, shown in FIG. 10 and depicted as an arrow pointing to a rectangle enclosing the words "LARGE PARTICLES". The remaining material that passed through the microfiltration unit is largely composed of casein micelles as well as dissolved proteins, salts and carbohydrates (not shown).

Further continuing this example of the purification of micelles formed in vivo in soybean as an embodiment, the material that passed through the microfiltration unit is then processed with an ultrafiltration unit that allows dissolved molecules lower than 100 nm in diameter to pass through while retaining casein micelles, shown in FIG. 10 and depicted as an arrow pointing to a rectangle enclosing the words "ULTRAFILTRATION". In some embodiments, continuous flow ultrafiltration with multiple filters in parallel are used to maximize flow rates. The soluble proteins, salts and minerals that passed through the ultrafiltration unit are discarded, shown in FIG. 10 and depicted as an arrow pointing to a rectangle enclosing the words "SOL. PROTEINS, SALTS, MINERALS".

Further continuing this example of the purification of micelles formed in vivo in soybean as an embodiment, the final output from this process is an aqueous liquid where the most common component after water is casein micelles, shown in FIG. 10 and depicted as an arrow pointing to a rectangle enclosing the words "CONCENTRATED MICELLES". These micelles (not shown) retain their shape and function such that they can be used in downstream processes such as in making synthetic milk or cheese.

As additional examples for FIG. 10, a method of isolating recombinant micelles from a seed of a plant produced can include cleaning, and deshelling or dehulling seeds, flaking cleaned seeds to 0.005-0.02 inch thickness, solvent extraction of oil from the flake, desolventizing the flake without cooking and collecting the defatted, clean flake, separating micelles into an aqueous slurry by hydrating, agitating and wet milling the flake, passing the slurry through a series of mesh screens to remove particulate above 0.5 mm in size and collecting the permeate, sonication of the permeate from previous step, microfiltration of the product from previous step to remove particulate above 2 um in size, ultrafiltration of the permeate from previous step using a device that allows particles >100 nm in diameter to pass through in the ultrafiltration permeate, collecting the retentate of previous step which contains concentrated recombinant micelles.

Continuing with this example, the method of isolating recombinant micelles from a seed further includes centrifuging the retentate of a previous step to separate the micelles from the remainder of the retentate. Also the method continues from the ultrafiltration step to passing the slurry through an ultrafiltration device and collecting a permeate containing protein and other molecules and a retentate containing micelles and thereafter adding a diafiltration fluid to the retentate at substantially the same rate that the permeate is collected and passing said retentate through the ultrafiltration device. Yet further the method continues where the seed is milled from at least one plant selected from the group of plants consisting of maize, rice, sorghum, cowpeas, soybeans, cassava, coyam, sesame, peanuts, peas, cotton and yams.

The resulting method, process, apparatus, device, product, and system is cost-effective, highly versatile, and accurate, and can be implemented by adapting components for ready, efficient, and economical manufacturing, application, production, and utilization. Another important aspect of an embodiment of the present disclosure is that it valuably supports and services the historical trend of reducing costs, simplifying systems, and increasing yield.

These and other valuable aspects of the embodiments of the present disclosure consequently further the state of the technology to at least the next level. While the disclosure has been described in conjunction with a specific best mode, it is to be understood that many alternatives, modifications, and variations will be apparent to those skilled in the art in light of the descriptions herein. Accordingly, it is intended to embrace all such alternatives, modifications, and variations that fall within the scope of the included claims. All matters set forth herein or shown in the accompanying drawings are to be interpreted in an illustrative and non-limiting sense.

What is claimed is:

1. A method of in vivo assembly of a recombinant micelle, comprising:
co-expressing at least two ruminant casein proteins in a plant cell;
wherein the at least two ruminant casein proteins comprise a κ-casein and at least one of an αS1-casein, an αS2-casein, or a β-casein; and
wherein the κ-casein and at least one of the αS1-casein, the αS2-casein, or the β-casein form the recombinant micelle in the plant cell.

2. The method in claim 1, wherein the at least two ruminant casein proteins are bovine casein proteins.

3. The method in claim 1, wherein co-expressing the at least two ruminant casein proteins in the plant cell comprises introducing a plasmid into the plant cell, wherein the plasmid comprises deoxyribonucleic acid (DNA) encoding ribonucleic acid (RNA) for the at least two ruminant casein proteins.

4. The method of in vivo assembly of a recombinant micelle in claim 1, wherein the recombinant micelle comprises:
1) an outer layer comprising the κ-casein, and
2) an inner matrix comprising at least one of the αS1-casein, the αS2-casein, or the β-casein.

5. The method of in vivo assembly of a recombinant micelle of claim 1, further comprising:
introducing at least one plasmid into the plant cell, wherein the at least one plasmid comprises at least one deoxyribonucleic acid (DNA) sequence encoding ribonucleic acid (RNA) for the at least two ruminant casein proteins comprising the κ-casein, the αS1-casein, the αS2-casein, or the β-casein.

6. A plant cell co-expressing at least two ruminant casein proteins, wherein the at least two ruminant casein proteins comprise a κ-casein and at least one of an αS1-casein, an αS2-casein, or a β-casein, and wherein the κ-casein and at least one of the αS1-casein, the αS2-casein, or the β-casein, form a recombinant micelle in the plant cell.

7. The plant cell in claim 6, wherein co-expressing the at least two ruminant casein proteins in the plant cell comprises introducing a plasmid into the plant cell, wherein the plasmid comprises deoxyribonucleic acid (DNA) encoding ribonucleic acid (RNA) for the at least two ruminant casein proteins.

8. A plant comprising the plant cell in claim 6.

9. The plant in claim 8, wherein the plant is at least one of maize, rice, sorghum, cowpea, soybean, cassava, coyam, sesame, peanut, peas, cotton, or yam.

10. The method in claim 1, wherein the recombinant micelle is assembled in an organelle of the plant cell.

11. The method in claim 10, wherein the organelle comprises a vacuole.

12. The method in claim 1, wherein the plant is soybean.

13. The plant cell in claim 6, wherein the plant is soybean.

14. The plant in claim 8, wherein the plant is soybean.

* * * * *

SEQUENCE LISTING

<160> NUMBER OF SEQ ID NOS: 35

<210> SEQ ID NO 1
<211> LENGTH: 600
<212> TYPE: DNA
<213> ORGANISM: Artificial Sequence
<220> FEATURE:
<223> OTHER INFORMATION: Codon optimized

<400> SEQUENCE: 1

```
aggcccaagc acccatcaa gcatcagggg ttgccacagg aagtcctcaa tgaaaatctg      60
ctgaggttct tcgtggctcc tttcccagaa gttttcggaa aggaaaaagt taacgagctc     120
agcaaagaca tcggctctga atccaccgaa gaccaagcaa tggaggacat taagcaaatg     180
gaagctgaga gtatatcctc atccgaagaa atcgtcccaa acagcgtaga acaaaagcat     240
attcagaaag aagatgttcc tagtgaaaga tacctcgggt atttggagca acttctgaga     300
ctgaaaaagt acaaagtgcc ccagctcgag atcgttccaa actccgccga agaacgtctg     360
catagtatga aggaggggat acatgcacaa cagaaggaac ccatgatcgg agttaaccag     420
gaactcgctt acttctaccc tgaactcttc aggcagtttt atcagcttga cgcttatccc     480
tccggtgctt ggtactatgt accacttgga acacaataca cagacgcacc atcattttct     540
gacataccca accctatcgg gtctgagaac agtgaaaaaa caacaatgcc tctgtggtaa     600
```

<210> SEQ ID NO 2
<211> LENGTH: 510
<212> TYPE: DNA
<213> ORGANISM: Artificial Sequence
<220> FEATURE:
<223> OTHER INFORMATION: Codon optimized

<400> SEQUENCE: 2

```
caggagcaga accaagaaca acctatcagg tgcgaaaagg atgagaggtt cttttccgat      60
aaaattgcaa agtacattcc tattcaatat gtactgtctc gctaccccag ttatggactt     120
aactactacc aacagaaacc cgttgccctt ataaacaatc agttcctccc ttatccttac     180
tatgcaaagc ctgctgccgt gcgtagtccc gcacagattc tccagtggca ggttctcagc     240
```

| | |
|---|---:|
| aatactgttc cgcaaaaag ctgtcaggct caacctacta ctatggcacg tcatcctcac | 300 |
| ccccatttga gctttatggc catccctcca agaagaacc aagataagac tgaaatccca | 360 |
| actataaaca caatcgcatc cggggagcct acctctactc ccactattga ggctgtcgaa | 420 |
| tctactgttg caactttgga agctagtccc gaagtcaccg agagcccccc tgagatcaac | 480 |
| accgtacagg ttacatctac cgctgtatga | 510 |

<210> SEQ ID NO 3
<211> LENGTH: 630
<212> TYPE: DNA
<213> ORGANISM: Artificial Sequence
<220> FEATURE:
<223> OTHER INFORMATION: Codon optimized

<400> SEQUENCE: 3

| | |
|---|---:|
| agggagctgg aagagctgaa cgtccctggc gaaatagtag agtccctcag ctcatcagaa | 60 |
| gagtccatta ctcgtattaa caaaaagatt gaaaagtttc agtcagaaga gcaacaacag | 120 |
| actgaggacg aactccaaga caagattcac cctttcgcac agacacagag tctggtctac | 180 |
| ccatttcctg gtcctattcc caattccctt ccccagaata tacctcccct cacccagact | 240 |
| cctgtggtgg tccccccatt cctccaacca gaggttatgg gtgtttctaa agtcaaagaa | 300 |
| gcaatggccc ctaagcacaa agagatgcca ttccccaagt atcccgttga gccctttacc | 360 |
| gagtctcaga gccttacact gaccgacgta gaaaatctcc atctcccact cccattgttg | 420 |
| caatcttgga tgcaccagcc ccatcagcct ttgccccccta ctgtcatgtt tcccccccag | 480 |
| agtgttctgt ccttgagcca aagcaaagtg ctccctgtgc cccagaaagc cgtaccttat | 540 |
| ccccaaagag acatgccaat acaggccttt tgctctacc aggagcctgt tctcggtccc | 600 |
| gtaagaggcc ctttccctat catcgtgtag | 630 |

<210> SEQ ID NO 4
<211> LENGTH: 624
<212> TYPE: DNA
<213> ORGANISM: Artificial Sequence
<220> FEATURE:
<223> OTHER INFORMATION: Codon optimized

<400> SEQUENCE: 4

| | |
|---|---:|
| aaaaacacta tggagcacgt aagctcatcc gaggagagta taatctccca ggaaacatat | 60 |
| aaacaagaaa aaaatatggc aattaaccca tccaaggaaa acctgtgttc caccttttgt | 120 |
| aaggaagtcg tgcgtaatgc taatgaagaa gagtattcaa tcggctccag ttcagaggag | 180 |
| tctgcagaag tagccacaga ggaggttaag attactgttg atgataaaca ctaccaaaag | 240 |
| gcccttaacg agataaatca gttctatcaa aaatttcctc aatatttgca atacttgtat | 300 |
| cagggaccta ttgttctcaa tccttgggat caggttaagc gtaacgccgt accaattaca | 360 |
| ccaactctca caggagca gctcagcacc tccgaggaaa actccaaaaa gacagtggat | 420 |
| atggagtcaa ctgaggtctt cacaaaaaag acaaagctca ccgaggaaga gaagaacaga | 480 |
| ctcaactttt tgaaaaaaat atcacaaaga taccaaaagt ttgcactgcc ccaatatctc | 540 |
| aagactgttt accaacacca aaaggctatg aagccctgga ttcaaccaaa gaccaaagtc | 600 |
| ataccctacg tgaggtattt gtaa | 624 |

<210> SEQ ID NO 5
<211> LENGTH: 612
<212> TYPE: DNA
<213> ORGANISM: Artificial Sequence

```
<220> FEATURE:
<223> OTHER INFORMATION: Codon optimized

<400> SEQUENCE: 5
cgtccgaaac atccaatcaa gcaccaaggc ctcccacagg aggtcctcaa cgaaaacctt      60
ttacgttttt ttgtggcacc cttccctgag gtcttcggaa aggaaaaagt gaatgaactt     120
tcaaaggaca ttggcagcga atccacggaa gaccaggcga tggaggatat taagcagatg    180
gaggctgaaa gtattagctc ttccgaggag atagttccta attccgtgga acaaaagcac    240
attcaaaaag aggatgtccc gagtgagaga tacctgggct atctcgaaca gcttctgaga    300
ctaaaaaagt ataaggtccc gcaactggaa attgttccaa atagcgccga gaaaggtta    360 cattccatga aagaaggcat tcatgctcag caaaaggaac ctatgatcgg agtaaaccag    420
gaacttgcct atttttaccc ggagttgttc cgtcagttct atcagttgga tgcatacca    480 tcagggcat ggtactatgt acctctcggt acccaataca cggacgctcc ttctttctcc    540
gatataccca atcccatagg tagcgaaaac tctgagaaaa caactatgcc cctctggcat    600
gacgaacttt ag                                                        612

<210> SEQ ID NO 6
<211> LENGTH: 522
<212> TYPE: DNA
<213> ORGANISM: Artificial Sequence
<220> FEATURE:
<223> OTHER INFORMATION: Codon optimized

<400> SEQUENCE: 6
caagaacaga atcaggagca acccattagg tgtgagaagg acgaaaggtt tttttcagac     60
aaaatcgcga aatacatacc tattcagtac gttctcagca gatacctag ttatggactt    120 aactactacc agcaaaagcc tgtggcattg ataaataacc agttccttcc gtacccgtac    180
tatgcgaaac cggcagcggt acgaagccca gcccagattt tgcaatggca ggtattgagt    240
aacaccgtcc cggcgaaaag ttgtcaagcg caaccgacca caatggcccg acaccgcat    300 ccacatctca gcttcatggc aatcccaccc aagaaaaacc aagataaaac tgaaataccg    360
acaataaaca ctatagcttc aggcgagcca actagcacac ccactattga agcggtagag    420
agtacggtcg caaccctaga ggcaagcccg gaagtgactg aatctccgcc ggaaattaac    480
accgtccagg taacctcaac agcggttcat gacgaactct ag                      522

<210> SEQ ID NO 7
<211> LENGTH: 639
<212> TYPE: DNA
<213> ORGANISM: Artificial Sequence
<220> FEATURE:
<223> OTHER INFORMATION: Codon optimized

<400> SEQUENCE: 7
cgtgaactag aagagcttaa tgtgcctggt gagatagtcg aaagtttgtc cagctcagaa     60
gaatcaatta cacgtatcaa caaaaaaata gaaaagtttc aatctgagga caacaacag    120 acagaggacg aattacaaga taaaatacac ccatttgctc agacgcaaag cttagtctat    180
ccattcccag gaccaattcc gaatagctta cctcaaaaca tcccgccgct cacgcagacc    240
cctgtagtcg tgccgccgtt tttacaaccc gaggtcatgg gcgtcagcaa ggtaaaagag    300
gcaatggctc ctaagcataa ggagatgcct ttccctaaat atcccgtcga gcctttcacc    360
gagagccaat cttaacctt aacggacgta gagaacctac atcttcctct accactgtta    420
```

-continued

| caatcctgga tgcatcagcc gcaccaacct cttccccta cagtaatgtt cccccgcag | 480 |
| tccgtcctat ctctctctca atccaaggtc ctaccagttc ctcagaaggc tgtccctac | 540 |
| cctcagcgag acatgccgat ccaggctttc ttgctatacc aagagccggt actaggccct | 600 |
| gtccgagggc cgtttccgat aattgtccac gatgaactt | 639 |

<210> SEQ ID NO 8
<211> LENGTH: 636
<212> TYPE: DNA
<213> ORGANISM: Artificial Sequence
<220> FEATURE:
<223> OTHER INFORMATION: Codon optimized

<400> SEQUENCE: 8

| aaaaacacta tggagcatgt gagcagctct gaggagtcca ttatatccca ggaaacatat | 60 |
| aaacaagaaa agaacatggc tattaacccg tcaaaggaga atctgtgttc cacgttctgt | 120 |
| aaggaagtgg tgaggaacgc taatgaggaa gagtactcaa tcggcagttc atccgaagaa | 180 |
| tctgctgagg tggcgacaga agaagttaag attactgtcg acgacaaaca ctaccagaag | 240 |
| gccctaaatg agataaatca attttatcag aagttcccgc agtatttgca atatctatat | 300 |
| caggggccaa tcgttctcaa tccatgggat caggtgaaaa gaaacgcagt acctatcaca | 360 |
| cctacgctga acagggaaca actgagcacc tctgaggaaa actcaaaaaa gaccgtagac | 420 |
| atggagtcca ctgaggtctt taccaagaaa acaaagctaa cagaggagga gaaaaatcga | 480 |
| ctgaattttc tgaagaaaat cagccagcgt tatcaaaagt cgctctccc tcagtaccta | 540 |
| aagacggtat atcaacacca aaaagctatg aagccgtgga tacagcccaa gacgaaagtg | 600 |
| attccatacg tgcgttatct tcacgatgaa ttatag | 636 |

<210> SEQ ID NO 9
<211> LENGTH: 675
<212> TYPE: DNA
<213> ORGANISM: Artificial Sequence
<220> FEATURE:
<223> OTHER INFORMATION: Codon optimized

<400> SEQUENCE: 9

| atgggttact ctaagacact ggttgctggc ctgtttgcca cacttctgct ggctcccgtg | 60 |
| gtgttggcca ctgatcccga tccacttcaa gacttctgcg tagctgacct cgatggtaaa | 120 |
| gctgtaagtg tcaacggcca tccttgcaag ccaatgtcaa aagcagggga cgatttcttg | 180 |
| ttttcctcta aactggctaa agctggtaac acttccaccc ctaatggtag tgctgtgaca | 240 |
| gagcttgacg ttgcagaatg gcccggaact aacactttgg gagtcagtat gaaccgtgtc | 300 |
| gattttgccc ctggggggac aaatccacct catattcacc cacgtgccac agaaaattgg | 360 |
| atagtcatga agggcgaact tctcgtgggc atccttggca gcttggactc aggcaataaa | 420 |
| ctttattccc gcgtagtcag ggccggtgag actttcttga ttcccagggg actgatgcac | 480 |
| ctgcagttca acgtaggaaa aactgaagcc agtatggtag tctccttcaa ttctcaaaat | 540 |
| cccggtattg tgttcgtccc cctcactctg ttctcctcta accccccaat cccaactccc | 600 |
| gtacttacca aggctcttag agtcgaggct ggagttgtag agctgttgaa gtcaaagttt | 660 |
| gcagccggat tttaa | 675 |

<210> SEQ ID NO 10
<211> LENGTH: 176
<212> TYPE: DNA
<213> ORGANISM: Artificial Sequence

```
<220> FEATURE:
<223> OTHER INFORMATION: This sequence has elements from Arabidopsis
      thaliana and Glycine max.

<400> SEQUENCE: 10
agagccagag agcagcctca gcaaaacagg tcgtgatatg attcaattag cttccgactc      60
attcatccaa ataccgagtc gccaaaattc aaactagact cgttaaatga atgaatgatg     120
cggtagacaa attggatcat tgattctctt tgatttgctg aggctgctct ctggct        176

<210> SEQ ID NO 11
<211> LENGTH: 1644
<212> TYPE: DNA
<213> ORGANISM: Glycine max

<400> SEQUENCE: 11
atggcgtcaa ttactttttc tcttcttcaa tttcatcgtg ctcctattct tctgctaatt      60
ctgctcgcgg gtttcggtca ctgccatatt ccgtcaaccc tcgaaggtcc ctttgatccc     120
gtcaccgttc cgttcgaccc cgccttgcgc ggcgtcgccg tcgacttgcc ggaaaccgat     180
cctcgagttc gccgccgcgt ccggggtttc gagcccgaac agatttcggt ttctctctct     240
acctcccatg actccgtttg gatatcttgg gttacagggg agttccaaat aggtctcgac     300
atcaagcctt tagaccctaa aactgtatca agtgttgttc aatatggaac ttcaagattt     360
gaattagtgc atgaagctag aggccagtct ctcatctaca accagctcta tcctttttgaa    420 ggccttcaga attacacatc tggaatcatc catcacgttc aactcaaagg attggaacca    480
agcacactat actattatca atgtggagat ccttcattgc aagccatgag tgatatatac    540
tatttcagga ccatgccaat ttctggttca aagagctacc caggcaaagt agctgtagta    600
ggagatcttg gtcttactta taatacaact actaccatcg tcacctgac tagtaatgaa     660 cctgatcttc ttctattgat tggtgatgta acctacgcga atctgtacct cacaaatgga    720
actggctctg attgttatag ttgctcgttt ccactaactc ctatacatga aacctaccag    780
cctcgatggg attattgggg aaggtttatg cagaatctag tttctaacgt tccaataatg    840
gtggtagaag gaaatcatga aatagaaaaa caggctgaaa acaggacatt tgtggcctac    900
agttctaggt ttgcattccc ctctcaagaa gtggatcttc atctctacatt ctactattct    960 ttcaatgctg gaggcattca ttttattatg cttgggcctt atattaacta tgataaaacg    1020
gctgaacaat acaagtggtt ggagagagat ctggaaaatg ttgatagatc aataactccc    1080
tggcttgtag ttacttggca tccaccatgg tatagttctt atgaagccca ttacagagaa    1140
gcagagtgca tgagggtgga gatggaggac ctattatacg catatggtgt ggatataata    1200
tttaatggac atgttcatgc ctatgagagg tcaaaccgag tttacaatta caatttagat    1260
ccatgtggtc ctgtatatat tacagttggg gatggggca acagagagaa gatggcaatc    1320
aaattcgcag acgagcctgg tcattgtccc gatccattaa gtactcctga tccttatatg    1380
ggtggctttt gtgcaacaaa ttttacgttt ggtacaaaag tgagtaagtt ttgttgggat    1440
cgccagccag attacagtgc tttcagagaa agtagctttg ctatgggat tctagaggtg    1500 aaaaatgaaa cttgggctt tgtggagttgg tatcgtaatc aggactctta caaggaagtt    1560
ggggatcaaa tttacatagt gagacaacct gatatatgcc ccatccatca aagggtgaac    1620
atagattgca ttgcttcgat ataa                                            1644

<210> SEQ ID NO 12
<211> LENGTH: 1284
```

```
<212> TYPE: DNA
<213> ORGANISM: Artificial Sequence
<220> FEATURE:
<223> OTHER INFORMATION: Codon optimized

<400> SEQUENCE: 12
atggtcccac ttgcaagtac caccaccggc accgggaccg ctaccggtac atcaactgca     60
gccgaacctt ccgccactgt gccatttgca agtacagatc caaaccccgt cctctggaat    120
gaaacatcag atccagcact tgtgaagcct gagcgcaatc agctcggggc tactatccag    180
ggtcctgata atctgcctat cgatttgcag aacccagatc tgttggctcc tcctaccact    240
gaccatggtt ttgtagggaa tgcaaagtgg ccattctcat ttagcaaaca aagacttcaa    300
accggcgggt gggcaagaca gcaaaatgaa gtcgttcttc ctctcgctac caatctcgct    360
tgtactaata tgaggctgga agccggggca attagagagc tccattggca taaaaacgcc    420
gaatgggctt acgtgttgaa aggtagtacc cagatttccg ctgtggacaa tgagggaagg    480
aactacatca gtactgtcgg tccaggcgat ctgtggtatt ccccccctgg aatcccccac    540
tcccttcaag ccaccgccga cgaccctgag gggtccgagt catttttggt gtttgatagt    600
ggagccttca tgatgacgg aacctttctt ctcaccgact ggctgagtca cgtccctatg    660
gaagtcattc tgaaaaattt tagggccaag aaccccgctg cttggtccca tatacccgcc    720
cagcagttgt atattttttcc cagtgagcct ccgccgata accagccaga ccccgtcagt    780
ccccagggaa ccgtccccct cccatattcc tttaatttct caagtgtgga acctacccag    840
tactcagggg gtaccgccaa aattgccgat agtacaactt taatattag tgtcgcaatc    900 gcagtggcag aagtaacagt tgagcctgga gcactcagag aacttcattg caccccacc     960 gaagatgagt ggacattctt catctcaggc aacgcacgcg tgactatttt cgcagcacaa   1020
agtgtagcca gtactttga ttaccagggc ggagatatag catatgttcc cgccagtatg   1080
ggccactacg tcgagaacat agggaatact accttgacct accttgaagt gttcaacaca   1140
gacagattcg ccgacgtgag tcttagccag tggctggccc tcacacctcc atccgttgtt   1200
caagcacacc tgaacctcga tgacgaaact ctggccgaac ttaagcagtt cgccaccaag   1260
gctacagtag tgggccccgt gaat                                           1284

<210> SEQ ID NO 13
<211> LENGTH: 1024
<212> TYPE: DNA
<213> ORGANISM: Glycine max

<400> SEQUENCE: 13
aaagaagtaa atcatgagct tttccaactc aacatctatt tttttctct caacctttttt    60 cacatcttaa gtagtctcac cctttatata tataacttat ttcttacctt ttacattatg   120
taacttttat caccaaaacc aacaacttta aattttatt aaatagactc cacaagtaac    180
ttgacactct tacattcatc gacattaact tttatctgtt ttataaatat tattgtgata   240
taatttaatc aaaataacca caaactttca taaaaggttc ttattaagca tggcatttaa   300
taagcaaaaa caactcaatc actttcatat aggaggtagc ctaagtacgt actcaaaatg   360
ccaacaaata aaaaaaaagt tgctttaata atgccaaaac aaattaataa acacttaca    420 acaccggatt ttttttaatt aaaatgtgcc atttaggata aatagttaat attttaata    480 attatttaaa aagccgtatc tactaaaatg attttttattt ggttgaaaat attaatatgt   540
ttaaatcaac acaatctatc aaaattaaac taaaaaaaaa ataagtgtac gtggttaaca   600
```

```
ttagtacagt aatataagag gaaaatgaga aattaagaaa ttgaaagcga gtctaatttt        660
taaattatga acctgcatat ataaaaggaa agaaagaatc caggaagaaa agaaatgaaa        720
ccatgcatgg tccctcgtc atcacgagtt tctgccattt gcaatagaaa cactgaaaca         780
cctttctctt tgtcacttaa ttgagatgcc gaagccacct cacaccatga acttcatgag        840
gtgtagcacc caaggcttcc atagccatgc atactgaaga atgtctcaag ctcagcaccc        900
tacttctgtg acgtgtccct cattcacctt cctctcttcc ctataaataa ccacgcctca        960
ggttctccgc ttcacaactc aaacattctc tccattggtc cttaaacact catcagtcat       1020
cacc                                                                    1024
```

<210> SEQ ID NO 14
<211> LENGTH: 1055
<212> TYPE: DNA
<213> ORGANISM: Glycine max

<400> SEQUENCE: 14

```
tttacaataa atactcaatt tatctttcac aatcaaaaga ttgagatgtt gtaagatctc         60 cgataaatata cttatatctt ttcatttatt acgttttcaa atttgaattt taatgtgtgt       120
tgtaagtata aatttaaaat aaaaataaaa acaattatta tatcaaaatg gcaaaaacat       180
ttaatacgta ttatttaaga aaaaaatatg taataaatata tttatatttt aatatctatt       240
cttatgtatt ttttaaaaat ctattatata ttgatcaact aaaatatttt tatatctaca       300
cttattttgc attttatca attttcttgc gtttttggc atatttaata atgactattc         360
tttaataatc aatcattatt cttacatggt acatattgtt ggaaccatat gaagtgtcca       420
ttgcatttga ctatgtggat agtgttttga tccaggcctc catttgccgc ttattaatta       480
atttggtaac agtccgtact aatcagttac ttatccttcc tccatcataa ttaatcttgg       540
tagtctcgaa tgccacaaca ctgactagtc tcttggatca taagaaaaag ccaaggaaca       600
aaagaagaca aaacacaatg agagtatcct ttgcatagca atgtctaagt tcataaaatt       660
caaacaaaaa cgcaatcaca cacagtggac atcacttatc cactagctga tcaggatcgc       720
cgcgtcaaga aaaaaaaact ggaccccaaa agccatgcac aacaacacgt actcacaaag       780
gtgtcaatcg agcagcccaa acattcacc aactcaaccc atcatgagcc cacacatttg       840
ttgtttctaa cccaacctca aactcgtatt ctcttccgcc acctcatttt tgtttatttc       900
aacacccgtc aaactgcatg ccaccccgtg gccaaatgtc catgcatgtt aacaagacct       960
atgactataa atatctgcaa tctcggccca ggttttcatc atcaagaacc agttcaatat      1020
cctagtacac cgtattaaag aatttaagat atact                                 1055
```

<210> SEQ ID NO 15
<211> LENGTH: 1045
<212> TYPE: DNA
<213> ORGANISM: Glycine max

<400> SEQUENCE: 15

```
ccttctcatc ctctctgaat attttgagtg ctcttcctag ttatctagta atgcatgaaa         60
ttaaacttac taaatgtttc ttcaatttaa agaaataatt gttatctgt ttcaattttt        120 ttaagagaat tttaaaaaga taattgtttc ggggagagag atataaaaaa gaaaagggag       180
aaatattaaa atgtactaaa taatatgata agaaaagaga gaaaaataaa agagaaaatt       240
tgtatatagt tataattatt catgtaataa ggattcatct ctcaactgaa aatatactta       300
atgcagaaga aaaaatcatt atttacaaac gttgagtctt gagtgggaaa agaggaggcg       360
```

```
ccgttactat acaatataag atcatagtac tgacaaaatg cacagtaaaa cagttcaaat    420
tgagaaggat tcttaacaca ccatagtatt taatatatat ctttacagag acaattatgc    480
tggaggattc aggcaaagat tatatattgt ggatttgttt tttaataatt aacgcatcat    540
atgaaagatc gatgatatat actaatggtt ataagaaaaa tatttaacag tttctataac    600
cttttctctt tatcttttac tgtaatatta tttattttat ttcacatttt taatcagctt    660
atctcattta taaacgaaat tgtataaaaa tatacatgat gaactgaata gaacaatatt    720
gatctgatat tctcatattg tataagagga tagactttga gacgcggaga atctgtagga    780
ggggaccatt cagagtgcct ccaattttgg tgttgttcat tgtaccattg caaatataaa    840
cgaagcatgc atgcttatgt atgaggtgta acaaaattgg aaacaatagc catgcaaggt    900
gaagaatgtc acaaactcag caaccettat tcattgacgt gtccctcagt cactctcctc    960
tcatacctat aaatcaccac tcctcatgtt ctttccaatt caccaactcc ttcaaactta   1020
attattaaca cttccttagt tcaat                                         1045
```

<210> SEQ ID NO 16
<211> LENGTH: 1186
<212> TYPE: DNA
<213> ORGANISM: Glycine max

<400> SEQUENCE: 16

```
gtctatttgc atgttcttct gcatggtatt aagaagttct tagagaatta atctaagtac     60 atttttttg gtctggatca gacatcatat ggatgctttc aaattcatgc gttggagatt    120
aattttactc ataataggta attatattaa ttaaaagaaa ttttacataa aaatacaaca    180
taaattattc cattaaatat attattccct gtgactacaa tgagataatc taagtgtatt    240
tgaaagtgga acagtagaaa ttataaaaat tgcaatgagt tgaataaaaa aggttggatt    300
aagaaagtaa tctaagtaca tttggaagtg gaatagtaga aataaaatta aatgagttga    360
aattgaaaat aattaaaaaa agtagggcta agaaatttct ccttcaactt catgatagca    420
aatattccat taggccattt gtagtttatg aatgagtata tataatcatg attttaggaa    480
ttcgatctgc tcgacacaac cgtgttacac tttttttaaa atgtcatcat aaaaataaaa    540
aataaaagac atgttataat taagaataag gtgatcagta taaaaataag taattttggg    600
aaatattaaa gttcaaaaaa gaactattga agaaagaat attattattt aaaaagagaa    660
aagaaaatga tgaaatgcta ttttcagtta aagaaaataa gaaaaaaaaa tacaagaat    720 aattcaatgc tggggctgta tatatgttta agatgataat taattttttt ttaaaaaaaa    780
gataagaatt aaatatttc tcctttaatt tctgaatcac ggttttggtt ctgataagac    840
actgattagt cacccatcaa atataatgaa ctaattctcc tattctattt caaaattttg    900
attatactta gattaatttt ctaatatact tggacctgtt tttcatgcag aagatgcaga    960
tatagctaga cagcacctag taatcgtgga accaacacca atgtccatat catgcatgtg   1020
tgccaccttt caaatgtaat ccagtagtaa aaaaagccat gacatgtaac tccacgacag   1080
agtaaaactc tcagaagtac ctctcgtttc atatctgcaa atcctctaat ataaataact   1140
cacttcacgg gttctttct cttcacagca aaacaatta ataaag                    1186
```

<210> SEQ ID NO 17
<211> LENGTH: 179
<212> TYPE: DNA
<213> ORGANISM: Glycine max

<400> SEQUENCE: 17

```
ctacgaaggg cgttgcggtt gagggtgcag cgagagaggg caacaccggc acactggaat      60
ggcttgttgt tagggttcca tgtctcaatg agccctcctt ctgactctat acggttatcc     120
ggtttgaggg cattgagttt ttggatctgg cactcgtttt gctgaggctg ctctctgga      179
```

<210> SEQ ID NO 18
<211> LENGTH: 1000
<212> TYPE: DNA
<213> ORGANISM: Glycine max

<400> SEQUENCE: 18

```
aaaatagtgt ttgattttttt gacacattat taagtgtttt attttttaagt ttaaaagcat      60
tggtatcctt tcataaaagg aggtaatctt atttaagtca aggagaatta ttatgggaaa     120
taaaaccttt tttttttaaag tgtttaatat aattatatac tcaaaattcg atttatgatt     180
aaatctaagt gacatttaaa aaaaattagt gtgaaaataa tttatatata attttgaaaa     240
atttatcatt aatttttttt tataaataaa tgttaattta ttagttttta ttataaatgt     300
gaatagaatg gattcgaagc agcaatttct ctctttctcc ttttccatgc caaccttata     360
tatggtgacg aactgcatat acagtaaaac agttcaaatt gagaaagatt ttaaacatca     420
tagtatttga tatatatctt ttacagagac aattatgctg caggagttag ataagattat     480
tgtggatgtc atttttcttt ttaatattta acgcattata taaaagatga tatagtatgg     540
ttataaaaaa attatttaac agtttataaa acctttttt ttatctttta cagtaatatt     600
atttatttta tttcacattt ttttcatatc cttatctcat ttataaagga aattaattgt     660
ataaaaaaaa tatgatgcac tgaatagaat gctgatctta ttgtataagg aggatagaat     720
ttgagacgcg gagaatctgt agaggggggac cattcagggt gcctgcaatt ttggtgttgt     780
tcatgtacgg ttgcagatat aaacgaagca tagcttatgt atgaggtgta acaaaattgg     840
aaacaatagc catgcaaggt gaagaatgtc ccaactcag aaacccttct tcattgacgt     900
gtccctcact cactctcctc tcttcactat aaatcgccac tcttcgtgtt ctccacttca     960
ccaactcctt caaacttatt aacactttcc ttagttcaat                          1000
```

<210> SEQ ID NO 19
<211> LENGTH: 146
<212> TYPE: DNA
<213> ORGANISM: Glycine max

<400> SEQUENCE: 19

```
tttctgtctc atttggcatt gcgtattggg aaaagcagaa ccccagtcac aacaagtgcc      60
tccgaagttg caatagcgag aaagactcct acaggaacca agcatgccac gctcgttgca     120
acctccttaa ggtggaggaa gaagaa                                          146
```

<210> SEQ ID NO 20
<211> LENGTH: 150
<212> TYPE: DNA
<213> ORGANISM: Glycine max

<400> SEQUENCE: 20

```
ttcttcttcc tccaccttaa ggaggttgca acgagcgtgg catgcttggt tcctgtagga      60
gtctttctcg ctattgcaac ttcggaggca cttgttgtga ctggggttct gcttttccca     120
atacgcaatg ccaaatgaga cagaaactga                                      150
```

<210> SEQ ID NO 21
<211> LENGTH: 114
<212> TYPE: DNA
<213> ORGANISM: Glycine max

<400> SEQUENCE: 21

```
atcgagaatt ttaaggttga gtgtcctaat gtgaagtaca ccgagactga gattcagtcc     60
gtgtacaact acgaaaccac cgaacttgtt cacgagaaca ggaatggcac ctat          114
```

<210> SEQ ID NO 22
<211> LENGTH: 114
<212> TYPE: DNA
<213> ORGANISM: Glycine max

<400> SEQUENCE: 22

```
ataggtgcca ttcctgttct cgtgaacaag ttcggtggtt tcgtagttgt acacggactg     60
aatctcagtc tcggtgtact tcacattagg acactcaacc ttaaaattct cgat          114
```

<210> SEQ ID NO 23
<211> LENGTH: 1081
<212> TYPE: DNA
<213> ORGANISM: Glycine max

<400> SEQUENCE: 23

```
acaaaattaa gaactgatac atcttgtttt ttgtcactga agataaacac gtgatctttg     60
gcaaaacata aaggccaaca aaacaaactt gtctcatccc tgaatgattc gaatgccatc    120
gtatgcgtgt cacaaagtgg aatacagcaa tgaacaaatg ctatcctctt gagaaaagtg    180
aatgcagcag cagcagcaga ctagagtgct acaaatgctt atcctcttga gaaaagtgaa    240
tgcagcggca gcagacctga gtgctatata caattagaca cagggtctat taattgaaat    300
tgtcttatta ttaaatattt cgtttttatat taatttttta aatttaatt aaatttatat    360
atattatatt taagacagat atatttattt gtgattataa atgtgtcact ttttcttttta    420
gtccatgtat tcttctattt tttcaattta acttttatt tttatttta agtcactctt     480
gatcaagaaa acattgttga cataaaacta ttaacataaa attatgttaa catgtgataa    540
catcatattt tactaatata acgtcgcatt ttaacgtttt tttaacaaat atcgactgta    600
agagtaaaaa tgaaatgttt gaaaaggtta attgcatact aactattttt tttcctataa    660
gtaatctttt tgggatcaa ttgtatatca ttgagatacg atattaaata tgggtacctt    720
ttcacaaaac ctaacccttg ttagtcaaac cacacataag agaggatgga tttaaaccag    780
tcagcaccgt aagtatatag tgaagaaggc tgataacaca ctctattatt gttagtacgt    840
acgtatttcc tttttttgttt agtttttgaa tttaattaat taaaatatat atgctaacaa    900
cattaaattt taaatttacg tctaattata tattgtgatg tataataaat tgtcaacctt    960
taaaaattat aaaagaaata ttaattttga taaacaactt ttgaaaagta cccaataatg   1020
ctagtataaa taggggcatg actccccatg catcacagtg caatttagct gaagcaaagc   1080
a                                                                  1081
```

<210> SEQ ID NO 24
<211> LENGTH: 179
<212> TYPE: DNA
<213> ORGANISM: Glycine max

<400> SEQUENCE: 24

```
tccagagagc agcctcagca aaacgagtgc cagatccaaa aactcaatgc cctcaaaccg     60
```

```
gataaccgta tagagtcaga aggagggctc attgagacat ggaaccctaa caacaagcca      120
ttccagtgtg ccggtgttgc cctctctcgc tgcaccctca accgcaacgc ccttcgtag       179

<210> SEQ ID NO 25
<211> LENGTH: 211
<212> TYPE: DNA
<213> ORGANISM: Solanum tuberosum

<400> SEQUENCE: 25
ccaattggta agtttctgct tctacctttg atatatatat aataattatc attaattagt      60
agtaatataa tatttcaaat attttttca aaataaaaga atgtagtata tagcaattgc       120
ttttctgtag tttataagtg tgtatatttt aatttataac ttttctaata tatgaccaaa     180
atttgttgat gtgcagttgg gaaattgggt t                                     211

<210> SEQ ID NO 26
<211> LENGTH: 57
<212> TYPE: DNA
<213> ORGANISM: Artificial Sequence
<220> FEATURE:
<223> OTHER INFORMATION: Codon optimized

<400> SEQUENCE: 26
atggctaagt tggttttttc tctctgtttt ttgctctttt ccggctgttg ctttgca         57

<210> SEQ ID NO 27
<211> LENGTH: 63
<212> TYPE: DNA
<213> ORGANISM: Arabidopsis thaliana

<400> SEQUENCE: 27
atggactcta aaagtttcct cctgctgttg ctccttttttt gcttcttatt tttgcacgac     60
gca                                                                    63

<210> SEQ ID NO 28
<211> LENGTH: 221
<212> TYPE: DNA
<213> ORGANISM: Agrobacterium tumefaciens

<400> SEQUENCE: 28
gaaccgcaac gttgaaggag ccactgagcc gcgggtttct ggagtttaat gagctaagca     60
catacgtcag aaaccattat tgcgcgttca aaagtcgcct aaggtcacta tcagctagca     120
aatatttctt gtcaaaaatg ctccactgac gttccataaa ttcccctcgg tatccaatta    180
gagtctcata ttcactctca actcgatcga ggggatctac c                         221

<210> SEQ ID NO 29
<211> LENGTH: 403
<212> TYPE: DNA
<213> ORGANISM: Cauliflower mosaic virus

<400> SEQUENCE: 29
tgagactttt caacaaagga taatttcggg aaacctcctc ggattccatt gcccagctat     60
ctgtcacttc atcgaaagga cagtagaaaa ggaaggtggc tcctacaaat gccatcattg     120
cgataaagga aaggctatca ttcaagatct ctctgccgac agtggtccca agatggacc     180 cccacccacg aggagcatcg tggaaaaaga gaggttcca accacgtcta caaagcaagt     240
ggattgatgt gacatctcca ctgacgtaag ggatgacgca caatcccact atccttcgca    300
agacccttcc tctatataag gaagttcatt tcatttggag aggacaacaa ttaccaacaa    360
```
caacaaacaa caaacaacat tacaattact atttacaatt aca                        403

<210> SEQ ID NO 30
<211> LENGTH: 1014
<212> TYPE: DNA
<213> ORGANISM: Glycine max

<400> SEQUENCE: 30
atcagaatta aactttaatt ctagttaatt agaaaattt aggtttaaat acaacttcag        60
tgatcttatt ttatttattc tgtaatttta gtctctttat tttgaaataa aaattttgat      120
ccttcaattt taaaaaattc acaattaatt ttgatttcat tttcaatttt gtcatttatt      180
tattttattt cttatatttt aattgaacaa ataatttatt gatgacactt taaatgaatt      240
ttttaggttt aagattaagt taaattaaaa taaaagcat aaaacataaa taaaattgag       300
aactaaacta aaattatatt ttaaaata aaaaatctc tatttctgaa ataggtgaac         360
taaaattacc aatagaaaaa aataattaaa tgataaactt tgaataatc tcactaatca       420 cttttaagat ctcttattca ataaattttt cttttacatt catagaactc atatccgaaa     480
cctaaggacc gaatcaatac cactcgatat gttgataaat aataattatt ttaaaatcta     540
aatctagtta aaataatttt tatttggttg aaaatgttaa tatctttata aaagtacagt     600
attacaagaa caaatgaga aagaaattga aattcagtct aatttataaa taatcaacct      660
gcatgtaaaa ggaaagaaag aagcgagcag gaagaaaaga aatgaaacca tgcatggtcc     720 cccaccccc aggacatcat gggtttctgc catttgcaat acaaacactg aaacaccttt      780
ctctttgtca cgtaatcgag attccgaagc caccttacac cattaactta atgaggtgta     840
agacagaagg gttccatagc catgcatact gaagaatgtc ttaagctcag cacccccactt   900 ctgagacgtg tccctcattc accttcctct cttccctata ataaccacg cctcaggttc     960 tccgcttcac aacacaaaca ttctctccat tgtccttga atataatact cagc           1014

<210> SEQ ID NO 31
<211> LENGTH: 403
<212> TYPE: DNA
<213> ORGANISM: Cauliflower mosaic virus

<400> SEQUENCE: 31
tgagactttt caacaaagga taatttcggg aaacctcctc ggattccatt gcccagctat       60
ctgtcacttc atcgaaagga cagtagaaaa ggaaggtggc tcctacaaat gccatcattg      120
cgataaagga aaggctatca ttcaagatct ctctgccgac agtggtccca agatggacc      180 cccacccacg aggagcatcg tggaaaaaga agaggttcca accacgtcta caaagcaagt     240
ggattgatgt gacatctcca ctgacgtaag ggatgacgca caatcccact atccttcgca     300
agacccttcc tctatataag gaagttcatt tcatttggag aggacaacaa ttaccaacaa     360
caacaaacaa caaacaacat tacaattact atttacaatt aca                       403

<210> SEQ ID NO 32
<211> LENGTH: 382
<212> TYPE: DNA
<213> ORGANISM: Agrobacterium tumefaciens

<400> SEQUENCE: 32
ttttcaaatc agtgcgcaag acgtgacgta agtatccgag tcagttttta ttttctact        60 aatttggtcg tttatttcgg cgtgtaggac atggcaaccg ggcctgaatt tcgcgggtat      120

```
tctgtttcta ttccaacttt ttcttgatcc gcagccatta acgactttg aatagatacg    180 ctgacacgcc aagcctcgct agtcaaaagt gtaccaaaca acgctttaca gcaagaacgg    240
aatgcgcgtg acgctcgcgg tgacgccatt tcgccttttc agaaatggat aaatagcctt    300
gcttcctatt atatcttccc aaattaccaa tacattacac tagcatctga atttcataac    360
caatctcgat acaccaaatc ga                                             382

<210> SEQ ID NO 33
<211> LENGTH: 720
<212> TYPE: DNA
<213> ORGANISM: Artificial Sequence
<220> FEATURE:
<223> OTHER INFORMATION: Original GFP sequence was from jellyfish. This
      has changes that increase the fluorescence of the protein as well
      as codon optimizations for expression in plants.

<400> SEQUENCE: 33
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccttcagcta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actcacggca tggacgagct gtacaagtaa    720

<210> SEQ ID NO 34
<211> LENGTH: 552
<212> TYPE: DNA
<213> ORGANISM: Artificial Sequence
<220> FEATURE:
<223> OTHER INFORMATION: Codon optimized

<400> SEQUENCE: 34
atgagcccag aacgacgccc ggccgacatc cgccgtgcca ccgaggcgga catgccggcg     60
gtctgcacca tcgtcaacca ctacatcgag acaagcacgg tcaacttccg taccgagccg    120
caggaaccgc aggagtggac ggacgacctc gtccgtctgc gggagcgcta tccctggctc    180
gtcgccgagg tggacggcga ggtcgccggc atcgcctacg cgggtccctg gaaggcacgc    240
aacgcctacg actggacggc cgagtcgacc gtgtacgtct ccccccgcca ccagcggacg    300
ggactgggct ccacgctcta cacccacctg ctgaagtccc tggaggcaca gggcttcaag    360
agcgtggtcg ctgtcatcgg gctgcccaac gacccgagcg tgcgcatgca cgaggcgctc    420
ggatatgccc ccgcggcat gctgcgggcg gccggcttca gcacgggaa ctggcatgac    480 gtgggtttct ggcagctgga cttcagcctg ccggtgccgc ccgtccggt cctgcccgtc    540 accgaaatct ga                                                        552

<210> SEQ ID NO 35
<211> LENGTH: 253
```

```
<212> TYPE: DNA
<213> ORGANISM: Agrobacterium tumefaciens

<400> SEQUENCE: 35
gatcgttcaa acatttggca ataaagtttc ttaagattga atcctgttgc cggtcttgcg      60
atgattatca tataatttct gttgaattac gttaagcatg taataattaa catgtaatgc     120
atgacgttat ttatgagatg ggtttttatg attagagtcc cgcaattata catttaatac     180
gcgatagaaa acaaaatata gcgcgcaaac taggataaat tatcgcgcgc ggtgtcatct     240
atgttactag atc                                                        253
```